United States Patent
Kuo

(10) Patent No.: US 11,104,736 B2
(45) Date of Patent: Aug. 31, 2021

(54) METHODS OF TREATING CANCER IN SUBJECTS HAVING DYSREGULATED LYMPHATIC SYSTEMS

(71) Applicant: Ensemble Group Holdings, Scottsdale, AZ (US)

(72) Inventor: Michael David Kuo, Scottsdale, AZ (US)

(73) Assignee: Ensemble Group Holdings, Scottsdale, AZ (US)

( * ) Notice: Subject to any disclaimer, the term of this patent is extended or adjusted under 35 U.S.C. 154(b) by 0 days.

(21) Appl. No.: 17/119,207

(22) Filed: Dec. 11, 2020

(65) Prior Publication Data

US 2021/0095033 A1 Apr. 1, 2021

Related U.S. Application Data

(63) Continuation of application No. 17/041,802, filed as application No. PCT/US2019/025197 on Apr. 1, 2019.

(60) Provisional application No. 62/649,048, filed on Mar. 28, 2018.

(51) Int. Cl.
*A61K 39/395* (2006.01)
*C07K 16/28* (2006.01)
*A61P 35/04* (2006.01)
*A61K 39/00* (2006.01)

(52) U.S. Cl.
CPC .......... *C07K 16/2818* (2013.01); *A61P 35/04* (2018.01); *A61K 2039/505* (2013.01); *C07K 2317/21* (2013.01); *C07K 2317/24* (2013.01); *C07K 2317/76* (2013.01)

(58) Field of Classification Search
None
See application file for complete search history.

(56) References Cited

U.S. PATENT DOCUMENTS

2021/0024633 A1 1/2021 Kuo

FOREIGN PATENT DOCUMENTS

| WO | 2016154068 | | 9/2016 |
| WO | WO2016154068 | * | 9/2016 |
| WO | 2017087280 | | 5/2017 |
| WO | WO2017087280 | * | 5/2017 |
| WO | 2017125532 | | 7/2017 |
| WO | 2018057303 | | 3/2018 |
| WO | 2018229487 | | 12/2018 |
| WO | 2019191764 | | 10/2019 |

OTHER PUBLICATIONS

Francis, D. et al., "Blockade of Immune Checkpoints in Lymph Nodes Through Locoregional Delivery Augments Cancer Immunotherapy", Sci Transl Med., 12(563):eaay3575, (2020).
International Application No. PCT/US2019/025197; International Preliminary Report on Patentability, dated Oct. 8, 2020; 8 pages.
International Application No. PCT/US2019/025197; International Search Report and Written Opinion of the International Searching Authority, dated Jun. 19, 2019; 8 pages.
Podgrabinska, S. et al., "Role of Lymphatic Vasculature in Regional and Distant Metastasis", Microvasc Res., 95:46-52, (2014).

* cited by examiner

*Primary Examiner* — Meera Natarajan
(74) *Attorney, Agent, or Firm* — Global Patent Group, LLC; Dennis Bennett; C A Schlecht

(57) ABSTRACT

Provided herein is a method for treating cancer in a patient in need thereof, wherein said cancer has a tumor proportion score (TPS) for programmed death receptor-1 (PD-1) or programmed death-ligand-1 (PD-L1) of 50% or less and said patient is negative for lymphatic dysfunction, comprising administering a therapeutically effective amount of an antagonist for immune checkpoint inhibition.

26 Claims, 8 Drawing Sheets

---------INDICATIONS AND USAGE---------
KEYTRUDA is a programmed death receptor-1 (PD-1)-blocking antibody indicated for the treatment of:
- patients with unresectable or metastatic melanoma. (1.1)
- patients with metastatic NSCLC whose tumors have high PD-L1 expression [(Tumor Proportion Score (TPS) ≥50%)] as determined by an FDA-approved test, with no EGFR or ALK genomic tumor aberrations, and no prior systemic chemotherapy treatment for metastatic NSCLC. (1.2)
- patients with metastatic NSCLC whose tumors express PD-L1 (TPS ≥1%) as determined by an FDA-approved test, with disease progression on or after platinum-containing chemotherapy. Patients with EGFR or ALK genomic tumor aberrations should have disease progression on FDA-approved therapy for these aberrations prior to receiving KEYTRUDA. (1.2)
- patients with recurrent or metastatic HNSCC with disease progression on or after platinum-containing chemotherapy. This indication is approved under accelerated approval based on tumor response rate and durability of response. Continued approval for this indication may be contingent upon verification and description of clinical benefit in the confirmatory trials. (1.3)
- adult and pediatric patients with refractory cHL, or who have relapsed after 3 or more prior lines of therapy. This indication is approved under accelerated approval based on tumor response rate and durability of response. Continued approval for this indication may be contingent upon verification and description of clinical benefit in the confirmatory trials. (1.4)

FIG. 4

METHODS OF TREATING CANCER IN SUBJECTS HAVING DYSREGULATED LYMPHATIC SYSTEMS

This application is a continuation application of U.S. application Ser. No. 17/041,802, filed Sep. 25, 2020, a national phase entry under 35 U.S.C. § 371, claiming the benefit of International Application No. PCT/US2019/025197, filed Apr. 1, 2019, and claiming the benefit of priority of U.S. Provisional Patent Application Ser. No. 62/649,048 filed Mar. 28, 2018, the disclosures of which are each incorporated by reference in their entireties for all purposes.

This disclosure relates to the field of treating cancer, particularly cancer in subjects having dysregulated lymphatic systems to whom an immune-modulating therapy is applied.

Patients who suffer from a dysregulated lymphatic system do not respond to immune-modulating therapies, which depend on immune cell priming, antigen presentation, or antigen trafficking. Patients with tumors treated with cancer immune-modulating therapy do not respond. By not responding, patients specifically rapidly progress from their tumor with minimal to no response period. Similarly, such patients have extremely poor overall survival compared to their counterparts who do not have dysregulation or dysfunction of their lymphatic system. Also, patients with lymphangitic carcinomatosis or lymphatic invasion do not respond to such cancer immune-modulating therapies, for lack of immune cell activation and immune cell priming.

As a broad class, immune-modulating therapies have remarkably benefited cancer patients in small and select groups. PD-1 and PD-L1 and related immune checkpoint inhibitors have remarkable response profiles in less than 30% of patients. Most studies positively correlate PD-1/PD-L1 staining in cancer patients and response, whether overall survival (OS), progression-free survival (PFS), objective response rate (ORR), or durable clinical response (DCR), irrespective of the pharmaceutical used (e.g., durvalumab, avelumab, nivolumab, atezolizumab, and pembrolizumab). The current art teaches that patients with certain tumor types consistently do not respond well, with less than 20% responding to these therapies. These cancers include non-small cell lung cancer (NSCLC), prostate cancer, breast cancers such as triple-negative, estrogen receptor-positive, and inflammatory types, nonhypermutated tumors, such as mismatch repair deficient (MMRD) tumors, microsatellite (MSI) instability positive or negative cancers, glioblastoma multiforme, and colon cancers.

The preceding examples of the related art and limitations related to that are intended to be illustrative and not exclusive. Other limitations of the related art will become apparent to those of skill in the art upon a reading of the specification and a study of the drawings.

The following embodiments and aspects thereof are described and illustrated in conjunction with compositions and methods, which are meant to be exemplary and illustrative, not limiting in scope. In various embodiments, one or more of the above-described problems have been reduced or eliminated, while other embodiments are directed to other improvements.

Provided herein is a method for treating cancer in a patient in need thereof, wherein said cancer has a tumor proportion score (TPS) for programmed death receptor-1 (PD-1) or programmed death-ligand-1 (PD-L1) of 50% or less and said patient is negative for lymphatic dysfunction, comprising administering a therapeutically effective amount of an antagonist for immune checkpoint inhibition.

In certain embodiments, the TPS is 30% or less, such as the TPS being 10% or less.

In certain embodiments, the lymphatic dysfunction is lymphangitic carcinomatosis (LC).

In certain embodiments, the immune checkpoint inhibition has a target chosen from PD-1, PD-L1, CTLA-4, LAG3, TIM-2, CD47, KIR, TIM3, CD30, OX40, IDO, and ICOS.

In certain embodiments, the immune checkpoint inhibition targets PD-1 or PD-L1.

In certain embodiments, the antagonist is chosen from afatinib dimaleate, alectinib, bevacizumab, carboplatin, ceritinib, crizotinib, docetaxel, doxorubicin, erlotinib, etoposide, everolimus, gefitinib, gemcitabine, mechlorethamine, methotrexate, necitumumab, nivolumab, osimertinib, paclitaxel, paclitaxel albumin-stabilized nanoparticles, pembrolizumab, pemetrexed, ramucirumab, topotecan, vinorelbine, pharmaceutically acceptable salts thereof, and combinations thereof.

In certain embodiments, the antagonist is chosen from bevacizumab, necitumumab, nivolumab, pembrolizumab, ramucirumab, pharmaceutically acceptable salts thereof, and combinations thereof.

In certain embodiments, the antagonist is pembrolizumab or pharmaceutically acceptable salts thereof.

In certain embodiments, the cancer is chosen from lung cancer, breast cancer, a cancer of the gastrointestinal tract, a cancer of unknown origin, head and neck cancer, bladder cancer, prostate cancer, skin cancer, kidney cancer, a primary brain tumor, ocular tumor, sarcoma, a cancer of primary soft tissue, mesenchymal cancer, bone cancer, ovarian cancer, cervical cancer, a tumor of the lymphatic system, leukemia, mismatch repair-deficient positive tumors (MMRD positive), and mismatch repair-deficient negative tumors (MMRD negative), and microsatellite (MSI) instability positive or negative cancers.

In certain embodiments, the cancer is lung cancer chosen from non-small cell lung cancer (NSCLC), squamous cell lung cancer, large cell lung cancer, small cell lung cancer, bronchogenic carcinoma, adenocarcinoma, neuroendocrine lung cancer, and bronchoalveolar lung cancer.

In certain embodiments, the cancer is breast cancer chosen from ductal carcinoma in situ (DCIS), invasive ductal carcinoma (IDC), lobular carcinoma (ILC), inflammatory breast cancer, lobular carcinoma in situ (LCIS), male breast cancer, Paget's disease of the nipple, and Phyllodes tumors of the breast.

In certain embodiments, the breast cancer is invasive ductal carcinoma chosen from tubular carcinoma of the breast, medullary carcinoma of the breast, mucinous carcinoma of the breast, papillary carcinoma of the breast, and cribriform carcinoma of the breast.

In certain embodiments, the cancer is breast cancer defined by hormone receptor status chosen from estrogen receptor-positive, estrogen receptor-negative, progesterone receptor-positive, progesterone receptor-negative, herceptin positive, herceptin negative, and combinations thereof.

In certain embodiments, the cancer is breast cancer defined by expression of a predefined set of genes chosen from mammaprint, oncotypeDX, intrinsic subtypes, and nanostring prosigna.

In certain embodiments, the cancer is a cancer of the gastrointestinal tract chosen from a tumor of the stomach, gastric cancer, duodenal cancer, small or large intestine cancer, colorectal cancer, anal cancer, liver cancer, pancreatic cancer, gall bladder cancer, cholangiocarcinoma, and neuroendocrine cancer.

In certain embodiments, the cancer is skin cancer chosen from basal cell cancer, squamous cell cancer, and melanoma.

In certain embodiments, the cancer is kidney cancer chosen from renal cell cancer and oncocytoma.

In certain embodiments, the cancer is a primary brain tumor, chosen from glioma, a tumor with gliomatous components, a tumor with neuronal components, a tumor with oligodendroglial components, oligodendroglioma, astrocytoma, and glioblastoma multiforme.

In certain embodiments, the cancer is a tumor of the lymphatic system selected from the group consisting of B cell lymphoma, T cell lymphoma, diffuse B cell lymphoma, and Hodgkin's lymphoma.

In certain embodiments, the cancer is leukemia chosen from acute lymphoblastic leukemia, acute myeloid leukemia, chronic lymphocytic leukemia, and chronic myelogenous leukemia.

In certain embodiments, the cancer is lung cancer, and the antagonist is chosen from afatinib dimaleate, alectinib, bevacizumab, carboplatin, ceritinib, crizotinib, docetaxel, doxorubicin, erlotinib, etoposide, everolimus, gefitinib, gemcitabine, mechlorethamine, methotrexate, necitumumab, nivolumab, osimertinib, paclitaxel, paclitaxel albumin-stabilized nanoparticles, pembrolizumab, pemetrexed, ramucirumab, topotecan, vinorelbine, pharmaceutically acceptable salts thereof, and combinations thereof.

In certain embodiments, the cancer is advanced cancer or metastatic cancer.

Also provided is a method for treating lung cancer in a patient in need thereof, which cancer has a tumor proportion score for programmed death receptor-1 (PD-1) or programmed death-ligand-1 (PD-L1) of 30% or less and said patient is negative for lymphangitic carcinomatosis (LC), comprising administering a therapeutically effective amount of an antagonist for immune checkpoint inhibition targeting PD-1 or PD-L1.

Further provided for treating lung cancer in a patient in need thereof, which cancer has a tumor proportion score for programmed death receptor-1 (PD-1) or programmed death-ligand-1 (PD-L1) of 30% or less and said patient is negative for lymphangitic carcinomatosis (LC), comprising administering a therapeutically effective amount of pembrolizumab or a pharmaceutically acceptable salt thereof.

The disclosure also provides a method for treating cancer in a patient in need thereof, by determining if said cancer has a tumor proportion score for programmed death receptor-1 (PD-1) or programmed death-ligand-1 (PD-L1) of 30% or less and confirming said patient is negative for lymphatic dysfunction, then administering a therapeutically effective amount of an antagonist for immune checkpoint inhibition.

The disclosure further provides a for treating cancer in a patient in need thereof, wherein said cancer has a tumor proportion score for programmed death receptor-1 (PD-1) or programmed death-ligand-1 (PD-L1) of 30% or less by administering a therapeutically effective amount of an antagonist for immune checkpoint inhibition.

Additional embodiments and features are in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which form a part of this disclosure.

BRIEF DESCRIPTION OF THE DRAWINGS

The disclosure will be readily understood by the following detailed description in conjunction with the accompanying drawings, wherein like reference numerals designate like structural elements. The drawings provide exemplary embodiments or aspects of the disclosure and do not limit the scope of the disclosure.

FIG. 4 is the FDA drug label for the PD-1 checkpoint inhibitor pembrolizumab superficially teaches the use of pembrolizumab in NSCLC patients only in patients with a TPS>=1%.

DETAILED DESCRIPTION

I. Methods for Treating Cancer

Provided method for treating cancer in a patient in need thereof, wherein said cancer has a tumor proportion score (TPS) for programmed death receptor-1 (PD-1) or programmed death-ligand-1 (PD-L1) of 50% or less and said patient is negative for lymphatic dysfunction. The method comprises administering a therapeutically effective amount of an antagonist for immune checkpoint inhibition.

Figure 1:
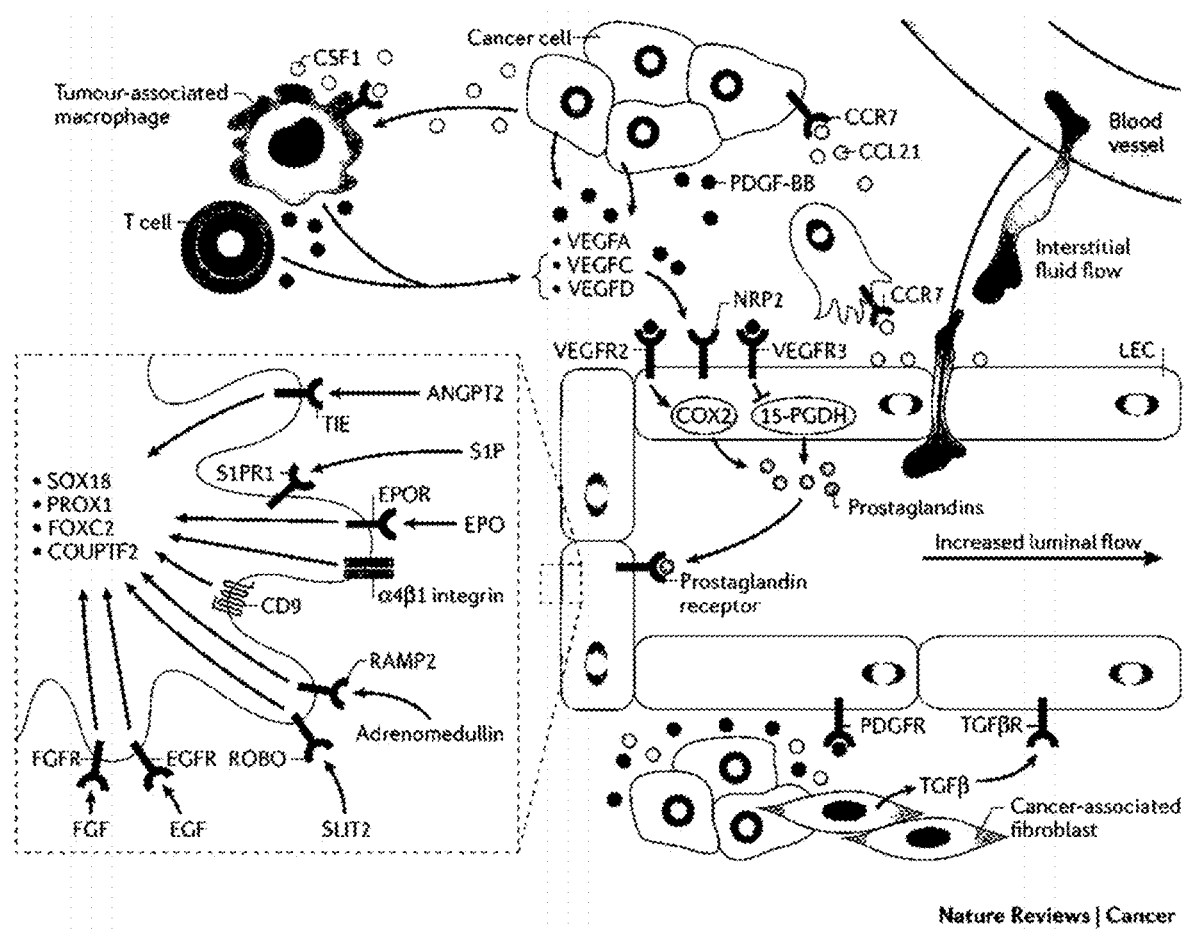
FIG. 1 is a schematic of general lymphatic biology showing molecules that modulate tumor lymphangiogenesis. See Stacker et al., "Lymphangiogenesis and lymphatic vessel remodeling in cancer," *Nature Reviews Cancer*, 14:159-172 (2014), incorporated herein by reference.

Molecules that modulate tumor lymphangiogenesis are shown in FIG. 1, with soluble ligands presented outside the cell, cognate receptors at the cell surface, and transcription factors in the nucleus. Vascular endothelial growth factor C (VEGFC) and VEGFD refer to the proteolytically processed, biologically active forms of these proteins. Most ligands that are shown promote lymphangiogenesis, while transforming growth factor-β (TGFβ) inhibits lymphangiogenesis. Other molecules are known to participate in lymphatic development in the embryo, such as collagen and calcium-binding EGF domain-containing protein 1 (CCBE1; not shown). A role in tumor lymphangiogenesis has not been shown. The interaction of tumor cells with lymphatic vessels can be promoted by interstitial fluid flow (which partly results from lymphatic drainage) via autologous chemotaxis involving chemokines, such as CC-chemokine ligand 21 (CCL21), and their receptors (CCR7 in the case of CCL21), expressed by tumor cells. Expression of CCL21 on lymphatic endothelial cells (LECs) can promote the entry of tumor cells into lymphatics via a CCR7-dependent mechanism. Producing lymphangiogenic growth factors, such as VEGFC and VEGFD, can drive the formation of new lymphatics and lymphatic enlargement near a tumor, which increases the surface area for the interaction of tumor cells with lymphatics. VEGFC can also promote tumor cell invasiveness in an autocrine manner, and it can upregulate the production of CCL21 on lymphatic vessels. The other abbreviations listed are 15-PGDH, 15-hydroxyprostaglandin dehydrogenase; ANGPT2, angiopoietin 2; COUPTF2, COUP transcription factor 2; COX2, cyclooxygenase 2; CSF1, colony-stimulating factor 1; EGF, epidermal growth factor; EGFR, EGF receptor; EPO, erythropoietin; EPOR, EPO receptor; FGF, fibroblast growth factor; FGFR, FGF receptor; FOXC2, forkhead box protein C2; PDGF-BB, platelet-derived growth factor BB; PDGFR, PDGF receptor; PROX1, prospero homeobox protein 1; RAMP2, receptor activity-modifying protein 2; SIP, sphingosine-1-phosphate; TGFβR, TGFβ receptor; VEGFR, VEGF receptor.

Figure 2:
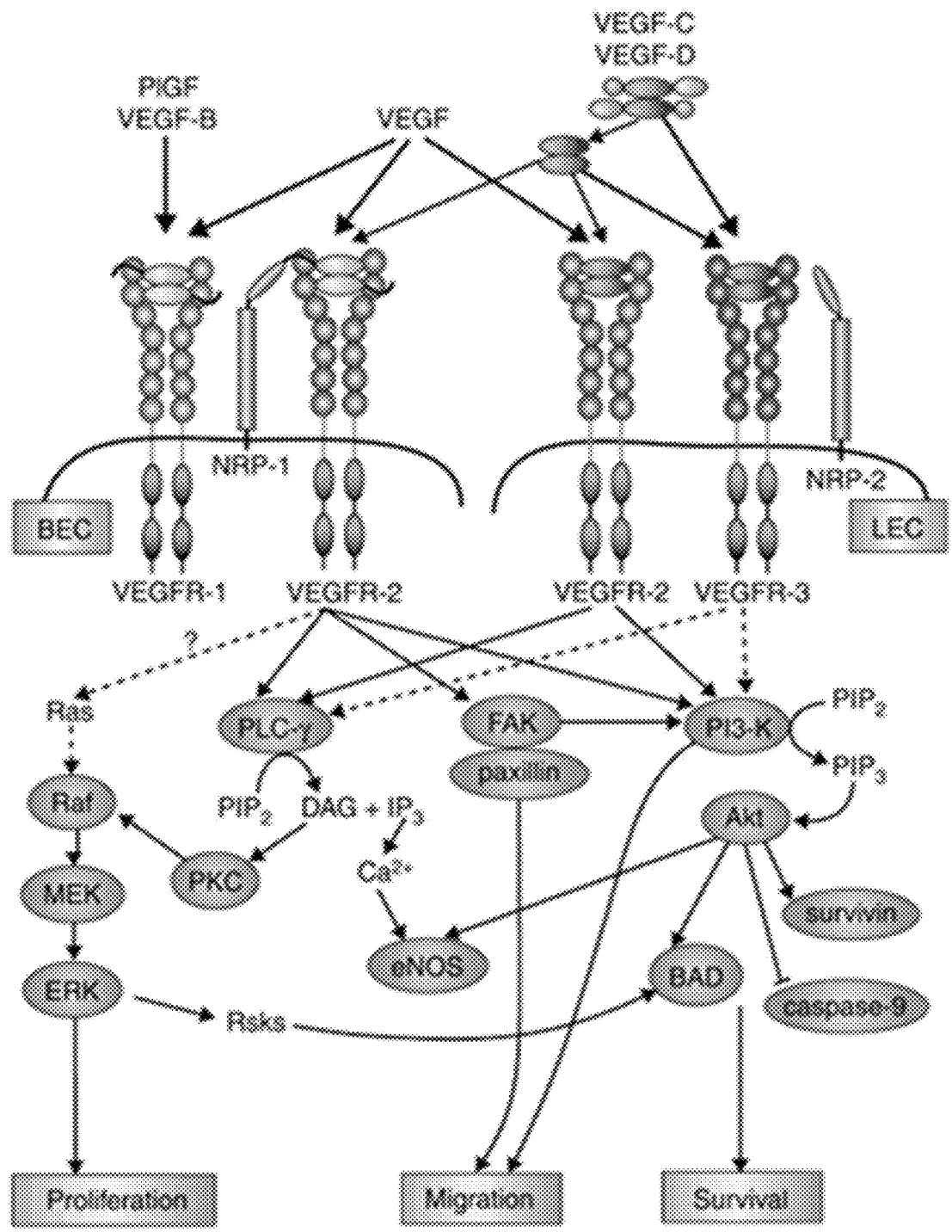
FIG. 2 is a schematic showing The VEGF family of ligands and their respective binding patterns to the VEGFR. See Karkkainen et al., "Lymphatic endothelium: a new frontier of metastasis research," *Nature Cell Biology*, 4:E2-E5 (2002).
Figure 3:
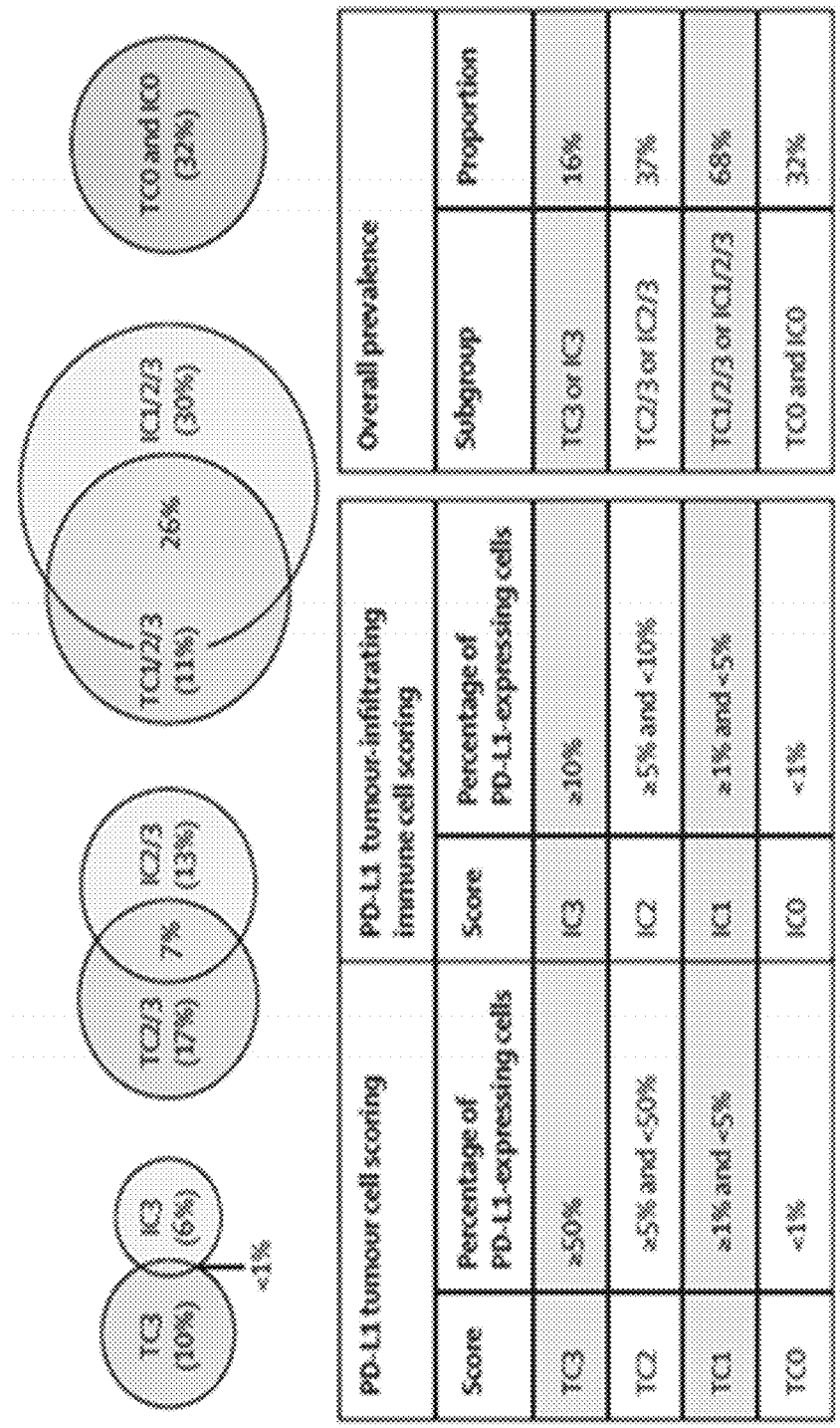
FIG. 3 is a flow chart showing the percentage of patients that are PD-L1+ and PD-L1-based on tumor proportion score (TPS>50%, TPS 1-49%, TPS<1%) in NSCLC.
Figure 5:
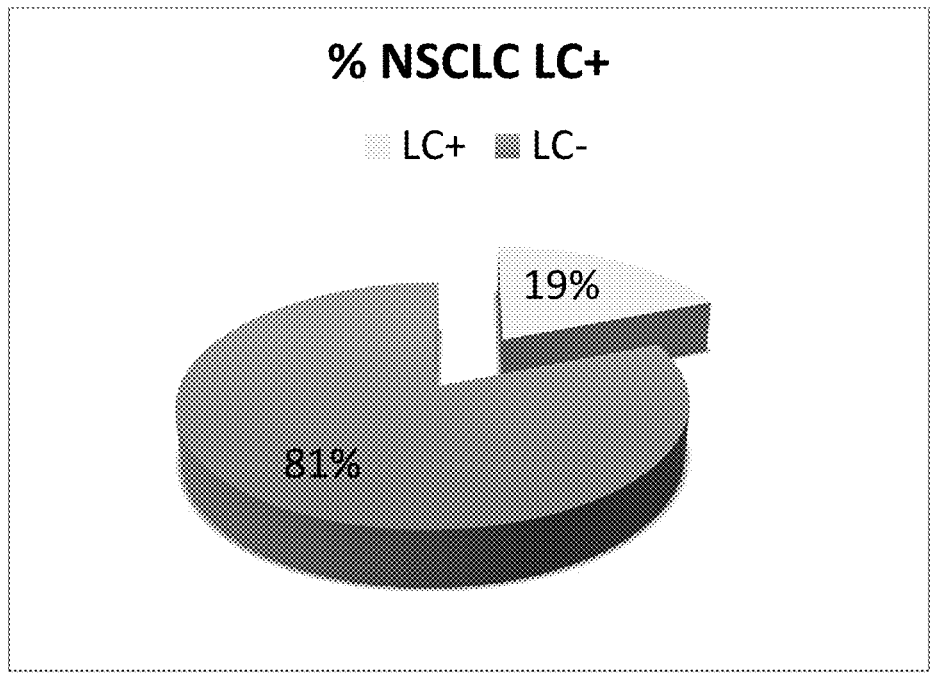
FIG. 5 is a pie chart showing the proportion of NSCLC tumors that are LC+ and LC-.
Figure 6:
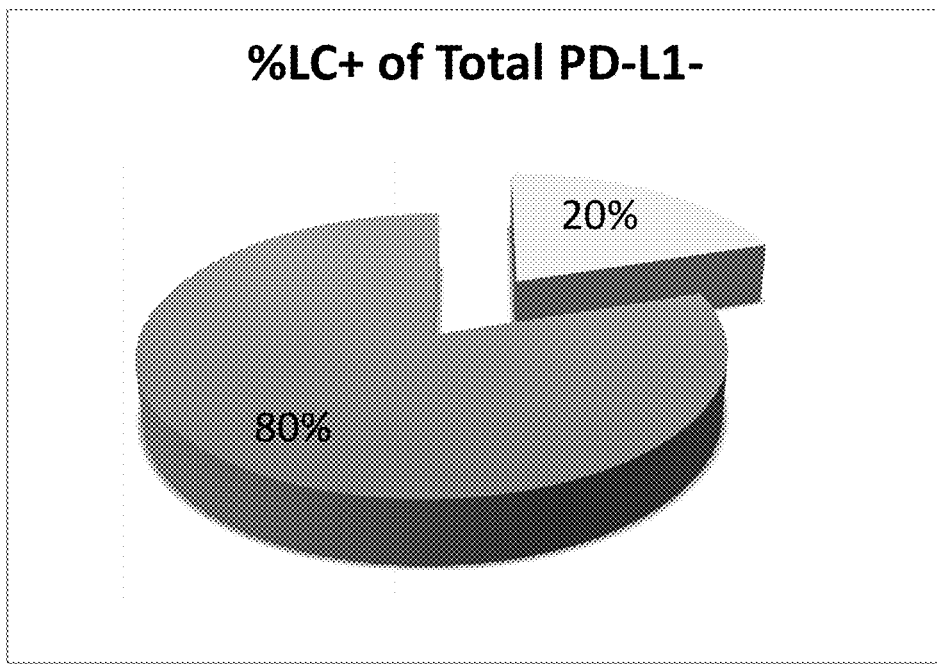
FIG. 6 us a pie chart showing the percentage of NSCLC patients with LC+/PD-L1-(20% blue)- and LC-/PD-L1- (80% orange). Thus, while it has been shown that only that those patients with very high TPS scores (>50% PD-L1 staining) will receive clinical benefit, and that patients with low TPS or negative (PD-L1 1-49% or (<1—approximately 30% of all patients have a TPS<1%)) do not derive benefit, this chart shows that of TPS<1%, only 20% are LC+ (TPS<1%/LC+), while the remaining 80% are LC- (TPS<1%/LC-). Thus, of the 30% not offered therapy because of presumed lack of benefit due to low TPS score (TPS<1%), 80% of these patients derive a real clinical benefit when stratified by LC status alone, which is a much stronger predictor of response independent of TPS (FIGS. 7-9).
Figure 7:
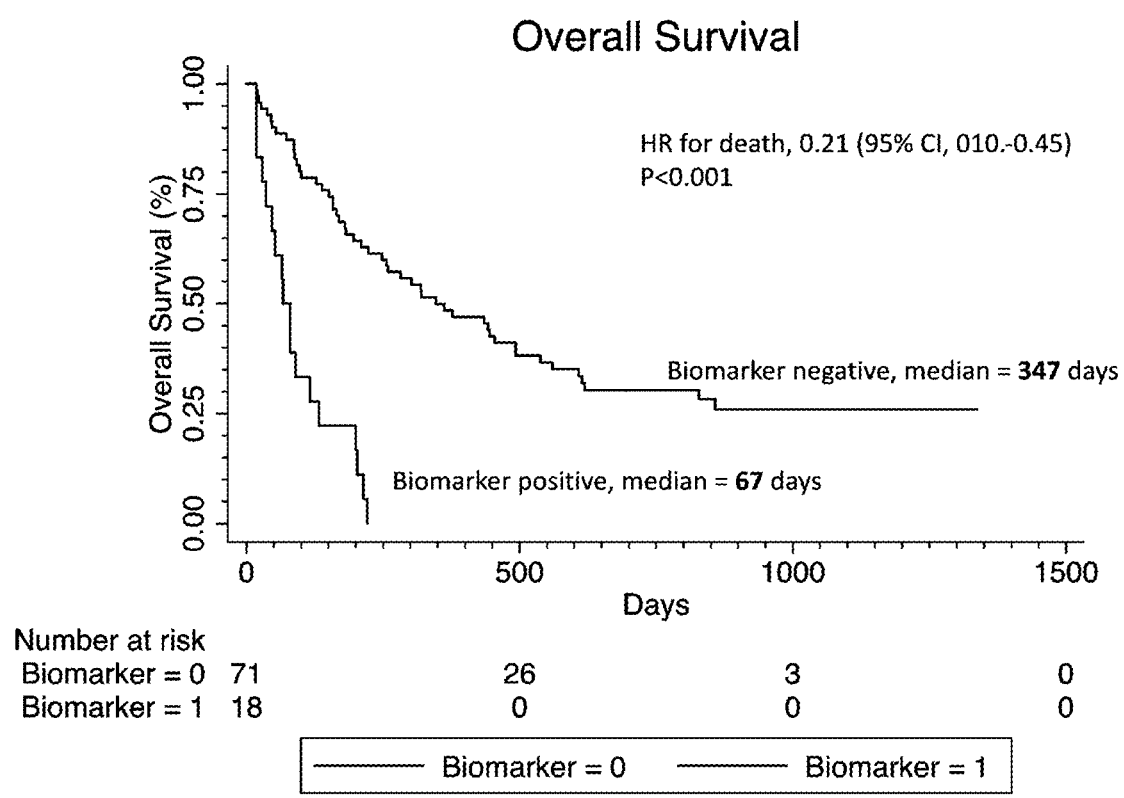
FIG. 7 is a Kaplan Meier plot showing a set of NSCLC patients treated with the PD-1 checkpoint inhibitor pembrolizumab (Keytruda™) stratified by LC+(biomarker positive "1" group OS=67 days) versus LC- (Biomarker negative "0" group OS=347 days). Patients that respond are defined by LC status independent of PD-L1 status (Cox proportional hazards analysis P<0.05).

The VEGF family of ligands and their respective binding patterns to the VEGFRs are shown in FIG. 2. VEGFR-1 and neuropilin-1 (NRP-1) are expressed in blood vascular ECs, VEGFR-3 and NRP-2 in lymphatic ECs, and VEGFR-2 occurs in both cell lineages. VEGFR-2 is the main signal-transducing receptor, as it activates several downstream signaling molecules (circles) and induces responses such as cell proliferation, migration, and survival. The protein kinase C (PKC)-mediated MEK/ERK pathway produces proliferation signals, in contrast to activating the PI3-kinase/Akt pathway, regulating cell survival. Focal adhesion kinase (FAK) and PI3-kinase migrate cells by stimulating the reorganization of actin and recruitment of actin-anchoring proteins to the focal adhesions. VEGF-C and VEGF-D are ligands for VEGFR-3, and they can induce LEC survival, migration, and growth via activation of the MEK/ERK and PI3-kinase/Akt pathways. However, after proteolytic cleavage, VEGF-C and VEGF-D can also bind and activate VEGFR-2 and stimulate both BECs and LECs. The distinct but overlapping receptor specificities and receptor expression patterns determine how VEGFs can differentially target both the blood vascular and/or lymphatic endothelium.

The art teaches that a patient's response to immune therapy depends on the PD-1 or PD-L1 expression or tumor neoantigen status. For example, hypermutant, microsatellite instability-high, DNA mismatch repair deficient (dMMR), or high neoantigen burden phenotype tumors respond strongly to checkpoint immune therapies. The cancers which are low in or do not express PD-1 or PD-L1 or are not hypermutant, not dMMR, microsatellite instability-low or normal, or have low neoantigen burdens, do not respond to checkpoint immune therapy. Breast cancer, particularly triple-negative (HER2−, ER−, PR−), ER+/HER2 negative, and inflammatory breast cancers, microsatellite instability low or normal, nonhypermutant/DNA mismatch repair low or normal colorectal cancers, and glioblastomas multiforme (GBMs), pancreatic cancer, sarcomas, and prostate cancers do not respond well to immune-modulating therapies. On the contrary, the present disclosure shows that the tumor types described above respond to immune checkpoint inhibition when treated in relation to lymphatic dysfunction, independent of PD-1/PD-L1, microsatellite instability degree, dMMR status, or neoantigen/hypermutant tumor status or type.

The art also suggests that tumors with elevated levels of lymphangiogenesis should have a better prognosis and better response to immune therapies because they have higher tumor immune cell infiltrates. To the contrary, following the present disclosure, such tumors should be treated with both immune modulation therapies, including immune checkpoint inhibitors, and a modulator of lymphatic biology, such as a VEGR-3 inhibitor, VEGF-C, VEGF-D, NRP 1, NRP 2, or CCPE1.

As such, therapies that modulate (stimulate or inhibit) immune biology at or downstream of this step are not effective monotherapies. They must be replaced with alternate therapies not dependent on these steps or mechanisms and treated with alternate therapies, or these immune-modulating therapies will either need to be independent of immune cell priming, antigen priming, or presentation, or the immune-modulating therapies dependent on these steps will need to be augmented or changed by agents that help to limit or overcome these issues. Further, cancer patients treated with immune-modulating therapies dependent on immune cell priming, antigen trafficking, or antigen presentation (e.g., immune checkpoint therapies) or patients that have dysregulated, dysfunctional or perturbed lymphatic systems can, as a class, all be augmented. Their clinical profiles improved through augmentation with such agents (antibody or antibody derivatives, or small molecular or small molecule derivatives) that regulate lymphatic angiogenesis.

Further, based on evaluating the status of the lymphatic system in the cancer subject, the potential treatment with immune-modulating therapy is assessed. If subjects are determined to have dysregulation of their lymphatic system by having abnormal lymphatic system features, then the treatment with any immune-modulating therapy that depends on efficient immune cell priming or antigen presentation is either aborted, deferred, or is augmented by a treatment method that modulates the lymphatic system to overcome or offset the dysfunctions.

Targeting lymphatics surrounding cancer therapy exclusively focuses on lymphatics as conduits for metastasis and as a means of limiting metastasis by preventing cancer cell spread along these conduits. The prior art focuses on these therapies in the context of providing more support around tumor-associated blood vessel angiogenesis by covering the vascular angiogenesis pathway that existing and marketed drugs do not cover. The art does not teach specific and highly selective inhibitors of lymphangiogenesis for augmenting or aiding immune modulation or immune therapies. The prior art also does not teach aiding immune checkpoint inhibitors as a principal means of augmenting the effects of these therapies, supporting or boosting immune therapies. Additionally, the prior art does not teach lymphangiogenesis inhibitors in combination with immune-modulating therapies in patients with lymphatic dysregulation, dysfunction, or perturbation.

The prior art does not teach treating patients with dysfunctional, dysregulated, or perturbed lymphatic systems characterized by lymphatic invasion and or lymphangitic carcinomatosis. While the prior art suggested anti-lymphangiogenic agents in ongoing clinical trials, the agents were selected solely for their known role as primary cancer therapies that target and inhibit vascular angiogenesis and do not selectively inhibit lymphangiogenesis. They are nonspecific agents with high general specificity for the entire VEGF family of receptors and many other angiogenesis-related targets (e.g., PDGF-BB, HGF, etc.), not specific and selective agents for VEGF-C/D and VEGFR 3. Additionally, the prior art does not teach lymphatic biology specific mediators for treating dysregulated lymphatics in the singular role of cancer immunotherapy for targeting lymphatic dysregulation so that immune therapies can more effectively function.

In a clinical setting, a major challenge is the treatment of established metastatic disease after the primary tumor has been surgically removed, eradicated by other means, or is unresectable. Following the present disclosure, established metastatic disease by blocking lymphangiogenesis using antagonists of VEGF-C receptors, VEGFR-3, and VEGFR-2 in combination with cancer immune-modulating therapies, which can include but are not limited to immune checkpoint inhibitors and in the setting of a dysregulated lymphatic system, or tumor-associated lymphatic invasion, lymphangitic carcinomatosis, or impaired antigen presentation, immune cell activation or priming alone or due to an impaired or dysregulated, dysfunctional or perturbed lymphatic system.

A. Lymphatic System

The lymphatic system comprises capillaries and larger collecting vessels continuously lined by endothelial cells, which return extravasated fluid and macromolecules from the interstitial space back to the blood circulation. Thus, the lymphatic system plays a vital role in regulating fluid, protein, and pressure equilibrium in tissues. By directing leukocytes and antigens from tissues to the lymph nodes, lymphatic vessels also have a key function in immune surveillance. Dysfunction of the lymphatic system results in lymphedema, a chronic and disabling condition for no treatments now available. Breast cancer treatment is associated with lymphedema, which often develops following surgical removal of lymph nodes and radiation therapy.

The lung is a common site for metastasis of many tumors, including common tumors such as breast, colorectal, prostate, bronchial, head-and-neck, and renal cancers. Pulmonary nodules are the most common manifestation of metastatic cancer in the lungs. Without wishing to be bound by theory, they are thought to be derived from tumor emboli which arrest in the lung capillaries and invade into the surrounding lung tissue. The involvement of pulmonary lymphatic vessels with cancer is less diagnosed because of imaging difficulties. At necropsy, metastases via pulmonary lymphatics and bronchial arteries are often seen.

Lymphatic dysfunction (LD) is a process maintained, supported, or regulated by the lymphatics inherently or acquire dysfunctionality, or dysregulation, including but not limited to processes involved in lymphangiogenesis, homeostatic regulation of the lymphatics vessels or secondary or tertiary lymphoid structures, lymphatic remodeling, lymphatic flow, transit or transfer of materials within or through the lymphatics, antigens or cells within, through or across lymphatic conduits, the maintenance, support or transformation of microenvironments including but not limited to the tumor microenvironment, and the secretion or expression of factors that induce or modulate cellular recruitment, migration or trafficking such as chemokines, cytokines, and other signaling molecules.

Involving lung lymphatics with cancer is a hallmark of a very aggressive metastatic disease, designated "lymphangitic carcinomatosis." LC is a type of LD in which obstruction of lymphatics to the primary or secondary draining nodes or other lymphatic structures or conduits either due to an extrinsic compression force or due to intrinsic invasion of the lymphatics with cells, often abnormal cell, or tumor cells, or due to hypertrophy or growth of supporting lymphatic tissue, cells or the lymphatic endothelium. The prognosis for a patient with this clinical picture is extremely poor; 50% of the patients die within 3 months of diagnosis. Although any cancer can cause lymphangitic spread, it most commonly results from tumors originating in the breast, stomach, pancreas, lung, or prostate. This phenomenon is also caused by primary pulmonary carcinoma, especially small cell carcinoma and adenocarcinoma. Because of the extremely aggressive nature of this disease, there is a great need for early diagnosis and treatment. Before the present disclosure, no treatment improved the outcome of patients with lymphangitic carcinomatosis.

Lymphangitic carcinomatosis is an aggressive disease that has been seen in association with many common metastatic cancers such as breast, gastric, pancreatic, prostate cancer, and others. Primary lung cancer can also present in the form of lymphangitic carcinomatosis, suggesting that targeting of VEGF-C/VEGFR-3 in lung cancer could be a treatment option for slowing the progression of lung cancer in combination with cancer immune-modulating therapies, which can include, but are not limited, to immune checkpoint inhibitors and in the setting of a dysregulated lymphatic system, or tumor-associated lymphatic invasion, lymphangitic carcinomatosis, or impaired antigen presentation, immune cell activation or priming alone or due to an impaired or dysregulated, dysfunctional or perturbed lymphatic system.

Clinically, lymphangitic carcinomatosis is characterized by malignant cells in the lymphatic vessels localized in the peri-bronchovascular area, the interlobular septa, and the centrilobular region. Associated pleural involvement is common. Edema resulting from blockage of lymphatic drainage and a desmoplastic reaction are common and can contribute to interstitial thickening. Hilar and mediastinal lymphadenopathy is present in 20-40% of patients, and pleural effusions are present in 30-50% of patients.

The lymphatic system may be assessed through imaging. The imaging may comprise one or more chosen from computer-assisted tomography (CAT), magnetic resonance imaging (MRI), positron emission tomography (PET), lymphoscintigraphy, and radiography of radiolabeled agents. The imaging may be computer-assisted tomography (CAT). The imaging may be magnetic resonance imaging (MRI). The imaging may be positron emission tomography (PET). The imaging may be lymphoscintigraphy. The imaging may be radiography of radiolabeled agents.

The lymphatic system may be assessed by measuring levels in a tissue sample of one or more first factors chosen from D2-40, podoplanin, CD34, and LYVE-1.

The first factor may be D2-40, a monoclonal antibody to an MW 40,000 O-linked sialoglycoprotein that reacts with a fixation-resistant epitope on lymphatic endothelium.

The first factor may be podoplanin.

The first factor may be CD34. Hematopoietic progenitor cell antigen CD34, also known as CD34 antigen, is a protein that in humans is encoded by the CD34 gene. CD34 is a cluster of differentiation in a cell surface glycoprotein and functions as a cell-cell adhesion factor. CD34 may also mediate the attachment of stem cells to bone marrow extracellular matrix or directly to stromal cells.

The first factor may be LYVE-1. Lymphatic vessel endothelial hyaluronan receptor 1 (LYVE1), also known as extracellular link domain containing 1 (XLKD1), is a Link domain-containing hyaladherin, a protein capable of binding to hyaluronic acid (HA), homologous to CD44, the main HA receptor. In humans, it is encoded by the LYVE1 gene.

The tissue sample may be concurrently stained for one or more second factors chosen from angiopoietin-1, angiopoietin-2, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PlGF, PLGF, TIE½, VEGF-A, VEGF-C, and VEGF-D to determine levels of these factors within lymphatics.

The second factor may be angiopoietin-1. The second factor may be angiopoietin-2.

The second factor may be BMP-9, also known as GDF2, which contains an N-terminal TGF-beta-like pro-peptide (prodomain) (residues 56-257) and a C-terminal transforming growth factor beta superfamily domain (325-428). GDF2 (BMP9) is secreted as a pro-complex consisting of the BMP9 growth factor dimer non-covalently bound to two BMP9 prodomain molecules in an open-armed conformation.

The second factor may be epidermal growth factor (EGF), which stimulates cell growth and differentiation by binding to its receptor, EGFR. Human EGF is a 6-kDa protein with 53 amino acid residues and three intramolecular disulfide bonds.

The second factor may be endoglin (ENG), which is a type I membrane glycoprotein on cell surfaces and is part of the TGF beta receptor complex. Endoglin is also commonly referred to as CD105, END, FLJ41744, HHT1, ORW, and ORW1. Endoglin has a crucial role in angiogenesis, therefore, making it an important protein for tumor growth, survival, and metastasis of cancer cells to other locations in the body.

The second factor may be endothelin-1 (ET-1), also known as preproendothelin-1 (PPET1), which is a potent vasoconstrictor that in humans is encoded by the EDN1 gene and produced by vascular endothelial cells. The protein encoded by this gene is proteolytically processed to release a secreted peptide termed endothelin 1. Endothelin 1 is one of three isoforms of human endothelin.

The second factor may be heparin-binding growth factor 1 (FGF-1) is a protein that in humans is encoded by the FGF1 gene.

The second factor may be heparin-binding growth factor 2 (FGF-2) is a protein that in humans is encoded by the FGF2 gene. FGF-1.

The second factor may be follistatin, also known as "activin-binding protein." Follistatin is a protein that in humans is encoded by the FST gene. Follistatin is an autocrine glycoprotein expressed in all tissues of higher animals.

The second factor may be a granulocyte-colony-stimulating factor (G-CSF or GCSF), also known as colony-stimulating factor 3 (CSF 3). G-CSF is a glycoprotein that stimulates the bone marrow to produce granulocytes and stem cells and release them into the bloodstream. Functionally, it is a cytokine and hormone, a type of colony-stimulating factor produced by many different tissues. The pharmaceutical analogs of naturally occurring G-CSF are called filgrastim and lenograstim. G-CSF also stimulates the survival, proliferation, differentiation, and function of neutrophil precursors and mature neutrophils.

The second factor may be the heparin-binding EGF-like growth factor (HB-EGF), a member of the EGF family of proteins that in humans is encoded by the HBEGF gene. The HB-EGF-like growth factor is synthesized as a membrane-anchored mitogenic and chemotactic glycoprotein. An epidermal growth factor produced by monocytes and macrophages, due to an affinity for heparin, is termed HB-EGF. It plays a role in wound healing, cardiac hypertrophy, and heart development and function. HB-EGF is an 87-amino acid glycoprotein that displays highly regulated gene expression. Ectodomain shedding results in the soluble mature form of HB-EGF, which influences the mitogenicity and chemotactic factors for smooth muscle cells and fibroblasts. The transmembrane form of HB-EGF is the unique receptor for diphtheria toxin and functions in juxtracrine signaling in cells. Both forms of HB-EGF participate in normal physiological processes and pathological processes, including tumor progression and metastasis, organ hyperplasia, and atherosclerotic disease. HB-EGF can bind two locations on cell surfaces: heparan sulfate proteoglycans and EGF-receptor, effecting cell to cell interactions.

The second factor may be a hepatocyte growth factor (HGF) or scatter factor (SF). HGF is a paracrine cellular growth, motility, and morphogenic factor. HGF is secreted by mesenchymal cells and targets and acts primarily upon epithelial cells and endothelial cells and acts on hemopoietic progenitor cells and T cells. It has a key role in embryonic organ development, specifically in myogenesis, adult organ regeneration, and wound healing.

The second factor may be insulin-like growth factor 1 (IGF-1), also called somatomedin C. IFG-1 is a protein that in humans is encoded by the IGF1 gene. IGF-1 has also been referred to as a "sulfation factor," and its effects were termed "nonsuppressible insulin-like activity" (NSILA).

The second factor may be interleukin 8 (IL-8 or chemokine (C-X-C motif) ligand 8, CXCL8) is a chemokine produced by macrophages and other cell types such as epithelial cells, airway smooth muscle cells, and endothelial cells. Endothelial cells store IL-8 in their storage vesicles, the Weibel-Palade bodies. In humans, the interleukin-8 protein is encoded by the CXCL8 gene. IL-8 is initially produced as a precursor peptide of 99 amino acids, which then undergoes cleavage to create several active IL-8 isoforms. In culture, a 72-amino acid peptide is a major form secreted by macrophages.

The second factor may be leptin. Leptin, the "satiety hormone," is a hormone made by adipose cells regulating energy balance by inhibiting hunger. Leptin is opposed by the actions of the hormone ghrelin, the "hunger hormone." Both hormones act on receptors in the arcuate nucleus of the hypothalamus to regulate appetite to achieve energy homeostasis. In obesity, a decreased sensitivity to leptin occurs, resulting in an inability to detect satiety despite high energy stores.

The second factor may be matrix metalloproteinase 2 (MMP-2). Also known as 72 kDa type IV collagenase and gelatinase A, MMP-2 is an enzyme that in humans is encoded by the MMP2 gene. The MMP2 gene is on chromosome 16 at position 12.2.

The second factor may be matrix metalloproteinase 9 (MMP-9). Also known as 92 kDa type IV collagenase, 92 kDa gelatinase, or gelatinase B (GELB), MMP-9 is a matrixin, a class of enzymes that belong to the zinc-metalloproteinases family involved in degrading the extracellular matrix. In humans, the MMP9 gene encodes for a signal peptide, a propeptide, a catalytic domain with inserted three repeats of fibronectin type II domain followed by a C-terminal hemopexin-like domain.

The second factor may be neuropilin-1 (NRP-1) is a protein that in humans is encoded by the NRP1 gene. In humans, the neuropilin 1 gene is at 10p11.22.

The second factor may be neuropilin-2 (NRP-2). NRP-2 is a protein that in humans is encoded by the NRP2 gene. This gene encodes a member of the neuropilin family of receptor proteins. The encoded transmembrane protein binds to SEMA3C protein {sema domain, immunoglobulin domain (Ig), short basic domain, secreted, (semaphorin) 3C} and SEMA3F protein {sema domain, immunoglobulin domain (Ig), short basic domain, secreted, (semaphorin) 3F}, and interacts with vascular endothelial growth factor (VEGF). This protein may play a role in cardiovascular development, axon guidance, and tumorigenesis. Multiple transcript variants encoding distinct isoforms have been identified for this gene.

The second factor may be a platelet-derived growth factor (PDGF) is one of many growth factors that regulate cell growth and division. PDGF plays a significant role in blood vessel formation (angiogenesis), the growth of blood vessels from already-existing blood vessel tissue, mitogenesis, i.e., proliferation, of mesenchymal cells such as fibroblasts, osteoblasts, tenocytes, vascular smooth muscle cells, and mesenchymal stem cells as well as chemotaxis, the directed migration, of mesenchymal cells. Platelet-derived growth factor is a dimeric glycoprotein that can be composed of two A subunits (PDGF-AA), two B subunits (PDGF-BB), or one of each (PDGF-AB).

The second factor may be phosphatidylinositol-glycan biosynthesis class F protein (PIGF).

The second factor may be a placental growth factor (PGF), a protein that in humans is encoded by the PGF gene. PGF is a member of the VEGF (vascular endothelial growth factor) sub-family. The main source of PGF during pregnancy is the placental trophoblast. PGF is also expressed in many other tissues, including the villous trophoblast.

The second factor may be tyrosine kinase with immunoglobulin-like and EGF-like domains 1 and 2 (TIE½), which is an angiopoietin receptor which in humans is encoded by the TIE1 gene.

The second factor may be vascular endothelial growth factor A (VEGF-A). The second factor may be vascular endothelial growth factor C (VEGF-C). The second factor may be vascular endothelial growth factor D (VEGF-D).

The lymphatic system may be assessed from elevated levels measured using a flow-cytometry-based multiplex assay or an enzyme-linked immunosorbent assay. The lymphatic system may be assessed from elevated levels measured using a flow-cytometry-based multiplex assay. The lymphatic system may be assessed from elevated levels measured using an enzyme-linked immunosorbent assay.

The lymphatic system may be assessed from expression levels measured by one or more techniques chosen from immunohistochemistry, gene expression profiling, and polymerase chain reaction (PCR)-based cDNA amplification of a lymphangiogenesis-regulating gene. The lymphatic system may be assessed from expression levels measured by immunohistochemistry. The lymphatic system may be assessed from expression levels measured by gene expression profiling. The lymphatic system may be assessed from expression levels measured by polymerase chain reaction (PCR)-based cDNA amplification of a lymphangiogenesis-regulating gene.

The lymphangiogenesis-regulating gene may be one or more selected from the group selected from angiopoietin-1, angiopoietin-2, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PIGF, PLGF, TIE½, VEGF-A, VEGF-C, and VEGF-D. The lymphangiogenesis-regulating gene may be angiopoietin-1. The lymphangiogenesis-regulating gene may be angiopoietin-2. The lymphangiogenesis-regulating gene may be BMP-9. The lymphangiogenesis-regulating gene may be EGF. The lymphangiogenesis-regulating gene may be endoglin. The lymphangiogenesis-regulating gene may be endothelin-1. The lymphangiogenesis-regulating gene may be FGF-1. The lymphangiogenesis-regulating gene may be FGF-2. The lymphangiogenesis-regulating gene may be follistatin. The lymphangiogenesis-regulating gene may be G-CSF. The lymphangiogenesis-regulating gene may be HB-EGF. The lymphangiogenesis-regulating gene may be HGF. The lymphangiogenesis-regulating gene may be IGF. The lymphangiogenesis-regulating gene may be IL-8. The lymphangiogenesis-regulating gene may be leptin. The lymphangiogenesis-regulating gene may be MMP-2. The lymphangiogenesis-regulating gene may be MMP-9. The lymphangiogenesis-regulating gene may be NRP 1. The lymphangiogenesis-regulating gene may be NRP 2. The lymphangiogenesis-regulating gene may be PDGF. The lymphangiogenesis-regulating gene may be PIGF. The lymphangiogenesis-regulating gene may be PLGF. The lymphangiogenesis-regulating gene may be TIE½. The lymphangiogenesis-regulating gene may be VEGF-A. The lymphangiogenesis-regulating gene may be VEGF-C. The lymphangiogenesis-regulating gene may be VEGF-D.

The lymphatic system may be assessed by profiling immune cells directly in a specimen by flow cytometry, mass spectrometry, cell labeling, or any combination thereof. The lymphatic system may be assessed by profiling immune cells directly in a specimen by flow cytometry. The lymphatic system may be assessed by profiling immune cells directly in a specimen by mass spectrometry. The lymphatic system may be assessed by profiling immune cells directly in a specimen cell labeling.

The lymphatic system may be assessed by measuring one or more markers selected from the group selected from angiopoietin-1, angiopoietin-2, heparin-binding factor midkine, BMP-9, EGF, endoglin, endothelin-1, FGF-1, FGF-2, follistatin, G-CSF, HB-EGF, HGF, IGF, IL-8, leptin, MMP-2, MMP-9, NRP 1, NRP 2, PDGF, PIGF, PLGF, TIE½, VEGF-A, VEGF-C, and VEGF-D. The marker may be angiopoietin-1. The marker may be angiopoietin-2. The marker may be heparin-binding factor midkine. The marker may be BMP-9. The marker may be EGF. The marker may be endoglin. The marker may be endothelin-1. The marker may be FGF-1. The marker may be FGF-2. The marker may be follistatin. The marker may be G-CSF. The marker may be HB-EGF. The marker may be HGF. The marker may be IGF. The marker may be IL-8. The marker may be leptin. The marker may be MMP-2. The marker may be MMP-9. The marker may be NRP 1. The marker may be NRP 2. The marker may be PDGF. The marker may be PIGF. The marker may be PLGF. The marker may be TIE½. The marker may be VEGF-A. The marker may be VEGF-C. The marker may be VEGF-D.

The dysregulated lymphatic system may be characterized by one or more chosen from abnormal lymphatic development, lymphatic proliferation, lymphangiogenesis, impaired lymphatic vessel function, dysregulated lymphatic vessel function, augmented tumor cell lymphatic infiltration, lymphangitic carcinomatosis, abnormal functioning or homeostatic regulation, lymphatic remodeling, physical pressure upon lymphatics, altered tumoral lymphatic development, altered tumoral lymphangiogenesis, and output blockage of lymphatic structures in lymphatic organs. The dysregulated lymphatic system may be characterized by abnormal lymphatic development. The dysregulated lymphatic system may be characterized by lymphatic proliferation. The dysregulated lymphatic system may be characterized by lymphangiogenesis. The dysregulated lymphatic system may be characterized by impaired lymphatic vessel function. The dysregulated lymphatic system may be characterized by dysregulated lymphatic vessel function. The dysregulated lymphatic system may be characterized by augmented tumor cell lymphatic infiltration. The dysregulated lymphatic system may be characterized by lymphangitic carcinomatosis. The dysregulated lymphatic system may be characterized by abnormal functioning or homeostatic regulation. The dysregulated lymphatic system may be characterized by lymphatic remodeling. The dysregulated lymphatic system may be characterized by physical pressure upon lymphatics. The dysregulated lymphatic system may be characterized by altered tumoral lymphatic development. The dysregulated lymphatic system may be characterized by altered tumoral lymphangiogenesis. The dysregulated lymphatic system may be characterized by the output blockage of lymphatic structures in lymphatic organs.

Further, based on evaluating the status of the lymphatic system in the cancer subject, the potential treatment with immune-modulating therapy is assessed. If subjects are determined to have dysregulation of their lymphatic system from abnormal lymphatic system features independent of PD-1 or PD-L1, then the treatment with any immune-modulating therapy that depends on efficient immune cell priming or antigen presentation is either aborted, deferred, or is augmented by a treatment method that modulates the lymphatic system to overcome or offset the dysfunctions.

B. Immune-Modulating Therapy

The immune-modulating therapy may be chosen from an antagonist for immune checkpoint inhibition, an agonist for immune co-stimulation signal, a stimulatory factor affecting immune cell priming and activation, a chemotactic agent, cytokine-related immune modulator, chemotherapeutic immune stimulation, radiotherapeutic immune stimulation, a vaccine, activation of an adaptive immune response, and activation of an innate immune response Immune-modulating therapy that works independent of immune cell priming and antigen presentation includes adoptive cell transfer and immune cell modification strategies, such as chimeric antigen receptor T cell (CAR-T) therapy. Here, immune cells are changed (1) intrinsically (in vivo modification which would include vaccination-based approaches and the like), (2) extrinsically via adoptive cell therapies or immune cell modification strategies, such as via CAR-T therapy, immune cell grafting, immune cell transplantation, or stem cell transplantation, and related strategies, and any combination of intrinsic or extrinsic modification.

The immune-modulating therapy may be an antagonist for immune checkpoint inhibition. The immune-modulating therapy may be an agonist for immune co-stimulation signal Immune-modulating therapy may be a stimulatory factor affecting immune cell priming and activation. Immune-modulating therapy may be a chemotactic agent. The immune-modulating therapy may be a cytokine-related immune modulator. Immune-modulating therapy may be chemotherapeutic immune stimulation. Immune-modulating therapy may be radiotherapeutic immune stimulation Immune-modulating therapy may be a vaccine. The immune-modulating therapy may be the activation of an adaptive immune response. The immune-modulating therapy may be the activation of an innate immune response.

The immune-modulating therapy may be an antagonist for immune checkpoint inhibition having a target chosen from PD-1, PD-L1, CTLA-4, LAG3, TIM-2, CD47, KIR, TIM3, and CD30.

The target may be programmed death receptor 1 (PD-1), also known as CD279 (cluster of differentiation 279). PD-1 is a cell surface receptor that downregulates the immune system and promotes self-tolerance by suppressing T cell inflammatory activity. PD-1 is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells). PD-1 inhibits the immune system. This prevents autoimmune diseases, but it can also prevent the immune system from killing cancer cells. Drugs that block PD-1, the PD-1 inhibitors, activate the immune system to attack tumors PD-1 is a cell surface receptor that belongs to the immunoglobulin superfamily and is expressed on T cells and pro-B cells. PD-1 binds two ligands, PD-L1 and PD-L2.

The target may be programmed death-ligand 1 (PD-L1). Also known as cluster of differentiation 274 (CD274) or B7 homolog 1 (B7-H1), PD-L1 is a protein that in humans is encoded by the CD274 gene. Programmed death-ligand 1 (PD-L1) is a 40 kDa type 1 transmembrane protein that may suppress the immune system during pregnancy, tissue allografts, autoimmune disease, and hepatitis. Normally, the immune system reacts to foreign antigens associated with exogenous or endogenous danger signals, which trigger a proliferation of antigen-specific CD8+ T cells and/or CD4+ helper cells. The binding of PD-L1 to PD-1 or B7.1 transmits an inhibitory signal that reduces the proliferation of these T cells and can also induce apoptosis, which is further mediated by a lower regulation of the gene Bcl-2.

The target may be cytotoxic T-lymphocyte-associated protein 4 (CTLA-4), also known as CD152 (cluster of differentiation 152). CTLA-4 is a protein receptor that, functioning as an immune checkpoint, downregulates immune responses. CTLA4 is constitutively expressed in regulatory T cells but only upregulated in conventional T cells after activation.

The target may be lymphocyte-activation gene 3 (LAG-3), a protein that in humans is encoded by the LAG3 gene. LAG3 is also designated CD223 (cluster of differentiation 223). LAG3 is a cell surface molecule with diverse biologic effects on T cell function. It is an immune checkpoint receptor.

The target may be T cell immunoglobulin and mucin domain family 2 (TIM-2) for family 3 (TIM3).

The target may be a Cluster of Differentiation 47 (CD47), also known as integrin associated protein (IAP). CD47 is a transmembrane protein that, in humans, is encoded by the CD47 gene. CD47 belongs to the immunoglobulin superfamily and partners with membrane integrins, and binds the ligands thrombospondin-1 (TSP-1) and signal-regulatory protein alpha (SIRPα). This is because the protein IAP produced by CD-47 acts as a don't-eat-me signal to the immune system and drives organ fibrosis. CD47 is involved in many cellular processes, including apoptosis, proliferation, adhesion, and migration. Furthermore, it plays a key role in immune and angiogenic responses. CD47 is ubiquitously expressed in human cells and is overexpressed in many different tumor cells. Expression in equine cutaneous tumors has been reported as well.

The target may be killer-cell immunoglobulin-like receptors (KIR), a family of type I transmembrane glycoproteins expressed on the plasma membrane of natural killer (NK) cells, and a minority of T cells.

The target may be CD30. CD30, also known as TNFRSF8, is a cell membrane protein of the tumor necrosis factor receptor family and tumor marker. This receptor is expressed by activated, but not by resting, T, and B cells. TRAF2 and TRAF5 can interact with this receptor and mediate the signal transduction that leads to activating NF-kappaB. It is a positive regulator of apoptosis, limits the proliferative potential of autoreactive CD8 effector T cells, and protects the body against autoimmunity. Two alternatively spliced transcript variants of this gene encoding distinct isoforms have been reported.

The immune-modulating therapy may be an agonist for immune co-stimulation signal having a target chosen from CD137/41BB, 41BBL, OX40, CD27, CD40/CD40L/cd40/CEA-CD3CD, and STING.

The target may be CD137/41BB. CD137 is a member of the tumor necrosis factor (TNF) receptor family Its alternative names are tumor necrosis factor receptor superfamily member 9 (TNFRSF9), 4-1BB, and induced by lymphocyte activation (ILA). CD137 can be expressed by activated T cells, but on CD8 than on CD4 T cells. Also, CD137 expression is found on dendritic cells, B cells, follicular dendritic cells, natural killer cells, granulocytes, and cells of blood vessel walls at sites of inflammation.

The target may be 4-1BB, a type 2 transmembrane glycoprotein belonging to the TNF superfamily, expressed on activated T lymphocytes. 41BBL is the ligand for 4-1BB.

The target may be OX40. Tumor necrosis factor receptor superfamily, member 4 (TNFRSF4), also known as CD134 and OX40 receptor, is a member of the TNFR-superfamily of receptors not constitutively expressed on resting naïve T cells, unlike CD28. OX40 is a secondary co-stimulatory immune checkpoint molecule, expressed after 24 to 72 hours following activation; its ligand, OX40L, is also not expressed on resting antigen-presenting cells but is following their activation. Expression of OX40 is dependent on full activation of the T cell; without CD28, expression of OX40 is delayed and of fourfold lower levels.

ICOS, or CD278, is the inducible T-cell costimulatory, an immune checkpoint protein that in humans is encoded by the ICOS gene. ICOS is a CD28-superfamily costimulatory molecule that is expressed on activated T cells. It is thought to be important for $T_h2$ cells.

The target may be a Cluster of Differentiation 27 (CD27), a member of the tumor necrosis factor receptor superfamily, and a co-stimulatory immune checkpoint molecule. The protein encoded by this gene is a member of the TNF-receptor superfamily. This receptor is needed for the generation and long-term maintenance of T cell immunity. It binds to ligand CD70 and regulates B-cell activation and immunoglobulin synthesis. This receptor transduces signals that lead to activating NF-κB and MAPK8/JNK. Adaptor proteins TRAF2 and TRAF5 have been shown to mediate the signaling process of this receptor. CD27-binding protein (SIVA), a proapoptotic protein, can bind to this receptor and induces apoptosis by this receptor.

The target may be a Cluster of Differentiation 40 or its ligand CD40/CD40L/cd40/CEA-CD3CD. CD40 is a costimulatory protein found on antigen-presenting cells and is needed for their activation. Binding CD154 (CD40L) on TH cells to CD40 activates antigen-presenting cells and induces various downstream effects. Deficiency can cause Hyper-IgM syndrome type 3.

The target may be a stimulator of interferon genes (STING), also known as transmembrane protein 173 (TMEM173) and MPYS/MITA/ERIS. STING is a protein that in humans is encoded by the TMEM173 gene.

The immune-modulating therapy may be a stimulatory factor affecting immune cell priming and activation chosen from CD28/B7.1, CD137/CD137L, OX40/OX40L, CD27/CD70, HVEM, GITR, CDN, ATB, HMGB1, TLR4, LR7, TLR 8, TLR9, MICA/MICB, B7-H2, B7-H3, B7-H4, and B7-½.

The stimulatory factor may be a Cluster of Differentiation 28 (CD28/B7.1) on proteins expressed on T cells that provide co-stimulatory signals for T cell activation and survival. T cell stimulation through CD28, in addition to the T-cell receptor (TCR), can provide a potent signal for producing various interleukins (IL-6 in particular). CD28 is the receptor for CD80 (B7.1) and CD86 (B7.2) proteins. When activated by Toll-like receptor (TLR) ligands, the CD80 expression is upregulated in antigen-presenting cells (APCs). The CD86 expression on antigen-presenting cells is constitutive (the expression is independent of environmental factors). CD28 is the only B7 receptor constitutively expressed on naive T cells. Association of the TCR of a naive T cell with MHC:antigen complex without CD28:B7 interaction results in an anergic T cell.

The stimulatory factor may be CD137/CD137L. CD137 is a member of the tumor necrosis factor (TNF) receptor family. Its alternative names are tumor necrosis factor receptor superfamily member 9 (TNFRSF9), 4-1BB, and induced by lymphocyte activation (ILA). CD137 is a co-stimulatory immune checkpoint molecule.

The stimulatory factor may be OX40/OX40L. The stimulatory factor may be CD27/CD70.

The stimulatory factor may be herpesvirus entry mediator (HVEM), also known as tumor necrosis factor receptor superfamily member 14 (TNFRSF14), a human cell surface receptor of the TNF-receptor superfamily.

The stimulatory factor may be GITR. Tumor necrosis factor receptor superfamily member 18 (TNFRSF18), also known as activation-inducible TNFR family receptor (AITR) or glucocorticoid-induced TNFR-related protein (GITR), is a protein that in humans is encoded by the TNFRSF18 gene. GITR is a co-stimulatory immune checkpoint molecule.

The stimulatory factor may be CDN. The stimulatory factor may be ATB.

The stimulatory factor may be a high mobility group box 1 protein, also known as high-mobility group protein 1 (HMG-1), and amphoterin, a protein that in humans is encoded by the HMGB1 gene. In the nucleus, HMGB1 interacts with nucleosomes, transcription factors, and histones. This nuclear protein organizes the DNA and regulates transcription. After binding, HMGB1 bends DNA, which aids the binding of other proteins. HMGB1 supports the transcription of many genes in interactions with many transcription factors. It also interacts with nucleosomes to loosen packed DNA and remodel the chromatin. Contact with core histones changes the structure of nucleosomes.

HMGB1 in the nucleus depends on posttranslational modifications. When the protein is not acetylated, it stays in the nucleus, but hyperacetylation on lysine residues causes it to translocate into the cytosol. HMGB1 has been shown to play an important role in helping the RAG endonuclease form a paired complex during V(D)J recombination. HMG-1 belongs to the high mobility group and contains the HMG-box domain.

The stimulatory factor may be toll-like receptor 4 (TLR4), a transmembrane member of the toll-like receptor family, belonging to the pattern recognition receptor (PRR) family Its activation leads to an intracellular signaling pathway NF-κB and inflammatory cytokine production responsible for activating the innate immune system. TLR 4 is most well-known for recognizing lipopolysaccharide (LPS), a component present in many Gram-negative bacteria (e.g., Neisseria spp.) and select Gram-positive bacteria. Its ligands also include several viral proteins, polysaccharides, and a variety of endogenous proteins such as low-density lipoprotein, beta-defensins, and heat shock protein. TLR4 has also been designated as CD284 (cluster of differentiation 284).

The stimulatory factor may be toll-like receptor 7 (TLR7), a protein that in humans is encoded by the TLR7 gene. TLR7 recognizes single-stranded RNA in endosomes, a common feature of viral genomes internalized by macrophages and dendritic cells. TLR7 recognizes single-stranded RNA of viruses such as HIV and HCV. TLR7 can recognize GU-rich single-stranded RNA. However, the presence of GU-rich sequences in the single-stranded RNA is not enough to stimulate TLR7.

The stimulatory factor may be toll-like receptor 8 (TLR8). Also known as cluster of differentiation 288 (CD288), TLR8 a protein that in humans is encoded by the TLR8 gene. TLR8 can recognize GU-rich single-stranded RNA. However, the presence of GU-rich sequences in the single-stranded RNA is not enough to stimulate TLR8. TLR8 recognizes G-rich oligonucleotides. TLR8 is an endosomal receptor that recognizes single-stranded RNA (ssRNA) and can recognize ssRNA viruses such as Influenza, Sendai, and Coxsackie B viruses. TLR8 binding to the viral RNA recruits MyD88 and activates the transcription factor NF-κB and antiviral response. TLR8 recognizes single-stranded RNA of viruses such as HIV and HCV.

The stimulatory factor may be toll-like receptor 9 (TLR9), also known as CD289 (cluster of differentiation 289). TLR9 is a member of the toll-like receptor (TLR) family TLR9 is an important receptor expressed in immune system cells, including dendritic cells, macrophages, natural killer cells, and other antigen-presenting cells. TLR9 preferentially binds DNA present in bacteria and viruses and triggers signaling cascades that lead to a pro-inflammatory cytokine response. Cancer, infection, and tissue damage can all modulate TLR9 expression and activation. TLR9 is also an important factor in autoimmune diseases, and there is active research into synthetic TLR9 agonists and antagonists that help regulate autoimmune inflammation.

The stimulatory factor may be a major histocompatibility complex (MHC) class I polypeptide-related sequence A (MICA) is a cell surface glycoprotein encoded by the MICA gene within the MHC locus. MICA is related to MHC class I and has a similar domain structure made up of an external α1α2α3 domain, a transmembrane segment, and a C-terminal cytoplasmic tail. However, MICA is not associated with β2-microglobulin, nor binds peptides as conventional MHC class I molecules do. MICA works as a stress-induced ligand for the NKG2D receptor. For example, the heat shock stress pathway regulates MICA expression, as the promoter heat shock element regulates the transcription of MICA. MICA is broadly recognized by NK cells, γδ T cells, and CD8+=αβ T cells, which carry NKG2D receptor on their cell surface. Because of NKG2D-MICA engagement, effector cytolytic responses of T cells and NK cells against epithelial tumor cells expressing MICA are started.

The stimulatory factor may be a major histocompatibility complex (MHC) class I polypeptide-related sequence B (MICB) is a protein that is encoded by the MICB gene within the MHC locus. MICB is related to MHC class I and has a similar domain structure made up of an external α1α2α3 domain, a transmembrane segment, and a C-terminal cytoplasmic tail. MICB is a stress-induced ligand for the NKG2D receptor. The heat shock stress pathway is involved in regulating MICB expression as transcription of MICB is regulated by the promoter heat shock element.

The stimulatory factor may be a B7 protein. B7 is a type of peripheral membrane protein found on activated antigen-presenting cells (APC) that, when paired with either a CD28 or CD152 (CTLA-4) surface protein on a T cell, can produce a costimulatory signal or a coinhibitory signal to enhance or decrease the activity of an MHC-TCR signal between the APC and the T cell, respectively. Binding the B7 of APC to CTLA-4 of T-cells causes inhibition of the activity of T-cells. There are two major types of B7 proteins: B7-1 or CD80 and B7-2 or CD86. However, it is not known if they differ significantly from each other. CD28 and CTLA-4 each interact with both B7-1 and B7-2. The stimulatory factor may be B7-H2. The stimulatory factor may be B7-H3. The stimulatory factor may be B7-H4. The stimulatory factor may be B7-½.

The immune-modulating therapy may be a chemotactic agent chosen from CX3CL1, CXCL9, CXCL10, CCL5, LFA1, ICAM1, selectin E, selectin P, selectin N, CXCR4, CCR2, CCL21, CCR5, CXCR1, CXCR2, CSF1R, and CCR4. The chemotactic agent may be a chemokine, a small protein that regulates cell trafficking of leukocytes. The chemokines also play fundamental roles in the development, homeostasis, and function of the immune system, and they have effects on cells of the central nervous system as well as on endothelial cells involved in angiogenesis or angiostasis.

The chemotactic agent may be CX3CL1. Fractalkine, also known as chemokine (C-X3-C motif) ligand 1, is a protein that in humans is encoded by the CX3CL1 gene. Fractalkine is a large cytokine protein of 373 amino acids; it has multiple domains and is the only known member of the CX3C chemokine family. The polypeptide structure of CX3CL1 differs from the typical structure of other chemokines.

The chemotactic agent may be chemokine (C-X-C motif) ligand 9 (CXCL9), a small cytokine belonging to the CXC chemokine family that is also known as monokine induced by gamma interferon (MIG). CXCL9 is a T-cell chemoattractant, which is induced by IFN-γ. It is closely related to two other CXC chemokines called CXCL10 and CXCL11, whose genes are near the gene for CXCL9 on human chromosome 4. CXCL9, CXCL10, and CXCL11 all elicit their chemotactic functions by interacting with the chemokine receptor CXCR3. Neutrophil collagenase/matrix metalloproteinase 8 (MMP-8) degrades CXCL9 and cleaves CXCL10 at two positions. Gelatinase B/matrix metalloproteinase 9 (MMP-9) degrades CXCL10 and cleaves CXCL9 at three different sites in its extended carboxy-terminal region.

The chemotactic agent may be C-X-C motif chemokine 10 (CXCL10), also known as interferon gamma-induced protein 10 (IP-10), or small-inducible cytokine B10. CXCL10 is an 8.7 kDa protein that, in humans, is encoded by the CXCL10 gene.

The chemotactic agent may be chemokine (C-C motif) ligand 5 (CCL5), a protein that in humans is encoded by the CCL5 gene. It is also known as RANTES (regulated on activation, normal T cell expressed and secreted).

The chemotactic agent may be lymphocyte function-associated antigen 1 (LFA-1), found on T-cells, B-cells, macrophages, neutrophils, and NK cells. LFA1 is involved in recruitment to the site of infection. It binds to ICAM-1 on antigen-presenting cells and functions as an adhesion molecule. LFA-1 is the first to bind T-cells to antigen-presenting cells and initially binds weakly. A signal from the T-cell receptor and/or the cytokine receptor changes the conformation and prolongs the cell contact, allowing the T-cell to proliferate. LFA-1/ICAM-1 interaction leads to further T cell differentiation. LFA-1 is part of the family of leukocyte integrins recognized by their common β-chains (β2, CD18). LFA-1 also has a distinct α-chain (αL, CD11a).

The chemotactic agent may be Intercellular Adhesion Molecule 1 (ICAM-1), also known as CD54 (Cluster of Differentiation 54). ICAM-1 is a protein that in humans is encoded by the ICAM1 gene, giving a cell surface glycoprotein typically expressed on endothelial cells and cells of the immune system. It binds to integrins of type CD11a/CD18 or CD11b/CD18 and is also exploited by rhinovirus as a receptor.

The chemotactic agent may be one or more selectins. The selectins (cluster of differentiation 62 or CD62) are a family of cell adhesion molecules (or CAMs). All selectins are single-chain transmembrane glycoproteins that share similar properties to C-type lectins due to a related amino terminus and calcium-dependent binding. Selectins bind to sugar moieties and are a type of lectin, cell adhesion proteins that bind sugar polymers. The chemotactic agent may be selectin E. The chemotactic agent may be selectin P. The chemotactic agent may be selectin N.

The chemotactic agent may be CXCR4. C-X-C chemokine receptor type 4 (CXCR-4), also known as fusion or CD184 (cluster of differentiation 184), is a protein that in humans is encoded by the CXCR4 gene.

The chemotactic agent may be C-C chemokine receptor type 2 (CCR2), also known as cluster of differentiation 192 (CD192), a protein that in humans is encoded by the CCR2 gene. CCR2 is a chemokine receptor. This gene encodes two isoforms of a receptor for monocyte chemoattractant protein-1 (CCL2), a chemokine that specifically mediates monocyte chemotaxis. Monocyte chemoattractant protein-1 is involved in monocyte infiltration in inflammatory diseases, such as rheumatoid arthritis, and the inflammatory response against tumors. The receptors encoded by this gene mediate agonist-dependent calcium mobilization and inhibition of adenylyl cyclase.

The chemotactic agent may be chemokine (C-C motif) ligand 21 (CCL21), a small cytokine belonging to the CC chemokine family. This chemokine is also known as 6Ckine (because it has six conserved cysteine residues instead of the four cysteines typical to chemokines), exodus-2, and secondary lymphoid tissue chemokine (SLC). The gene for CCL21 is on human chromosome 9. CCL21 elicits its effects by binding to a cell surface chemokine receptor known as CCR7.

The chemotactic agent may be C-C chemokine receptor type 5 (CCR5), also known as cluster of differentiation 195 (CD195), a protein on the surface of white blood cells involved in the immune system, as it acts as a receptor for chemokines. This is the process by which T cells are attracted to specific tissue and organ targets. Many forms of HIV, the virus that causes AIDS, initially use CCR5 to enter and infect host cells. Certain individuals carry a CCR5-432 mutation in the CCR5 gene, protecting them against these strains of HIV.

The chemotactic agent may be C-X-C motif chemokine receptor 1 (CXCR1), also known as interleukin 8 receptor, alpha (IL8RA), and a Cluster of Differentiation 181 (CD181). The protein encoded by this gene is a member of the G-protein-coupled receptor family. This protein is a receptor for interleukin 8 (IL8). It binds to IL8 with high affinity and transduces the signal through a G-protein-activated second messenger system. Knockout studies in mice suggested that this protein inhibits embryonic oligodendrocyte precursor migration in the developing spinal cord. This gene, IL8RB, a gene encoding another high-affinity IL8 receptor, and IL8RBP, a pseudogene of IL8RB, form a gene cluster in a region mapped to chromosome 2q33-q36. Stimulation of CXCR1 in neutrophils by its primary ligand, Interleukin 8, leads to neutrophil chemotaxis and activation.

The chemotactic agent may be CXCR2, also known as interleukin 8 receptor, beta (IL8RB). The protein encoded by this gene is a member of the G-protein-coupled receptor family. This protein is a receptor for interleukin 8 (IL8). It binds to IL8 with high affinity and transduces the signal through a G-protein-activated second messenger system (Gi/o-coupled). This receptor also binds to chemokine (C-X-C motif) ligand 1 (CXCL1/MGSA), a protein with melanoma growth stimulating activity, and is a major component for serum-dependent melanoma cell growth. Also, it binds ligands CXCL2, CXCL3, and CXCL5. The angiogenic effects of IL8 in intestinal microvascular endothelial cells are found to be mediated by this receptor. Knockout studies in mice suggested that this receptor controls the positioning of oligodendrocyte precursors in developing spinal cord by arresting their migration. This gene, IL8RA, a gene encoding another high-affinity IL8 receptor, and IL8RBP, a pseudogene of IL8RB, form a gene cluster in a region mapped to chromosome 2q33-q36. Mutations in CXCR2 cause hematological traits.

The chemotactic agent may be a colony-stimulating factor 1 receptor (CSF1R), also known as macrophage colony-stimulating factor receptor (M-CSFR), and CD115 (Cluster of Differentiation 115), a cell-surface protein encoded, in humans, by the CSF1R gene (also known as c-FMS). It is a receptor for a cytokine called colony-stimulating factor 1. The encoded protein is a single-pass type I membrane protein and acts as the receptor for colony-stimulating factor 1, a cytokine that controls the production, differentiation, and function of macrophages. This receptor mediates most, if not all, of the biological effects of this cytokine. Ligand binding activates CSF1R through a process of oligomerization and trans-phosphorylation. The encoded protein is a tyrosine kinase transmembrane receptor and a member of the CSF1/PDGF receptor family of tyrosine-protein kinases.

The chemotactic agent may be CCR4. C-C chemokine receptor type 4 is a protein that in humans is encoded by the CCR4 gene. CCR4 has also recently been designated CD194 (Cluster of Differentiation 194). The protein encoded by this gene belongs to the G protein-coupled receptor family. It is a receptor for the CC chemokines CCL2 (MCP-1), CCL4 (MIP-1), CCL5 (RANTES), CCL17 (TARC), and CCL22 (Macrophage-derived chemokine).

The immune-modulating therapy may be a chemotactic agent comprising a cytokine chosen from IL-1, IL-2, IL-4, IL-6, IL-7, IL-8, IL-13, IL-12, interferon gamma, IFNa, TNFa, CSF1, CSF1R, and GM-CSF.

The chemotactic agent may be the interleukin-1 family (IL-1 family), a group of 11 cytokines, which regulate immune and inflammatory responses to infections or sterile insults.

The chemotactic agent may be interleukin 2 (IL-2), a cytokine glycoprotein that stimulates the growth of T cell lymphocytes and provides other biochemical signaling to the immune system.

The chemotactic agent may be interleukin 4 (IL4, IL-4), a cytokine that induces differentiation of naive helper T cells (Th0 cells) to Th2 cells. Upon activation by IL-4, Th2 cells then produce more IL-4 in a positive feedback loop. Basophils may initially produce IL-4, thus inducing Th0 differentiation. IL-2 is closely related and has functions like interleukin 13.

The chemotactic agent may be interleukin 6 (IL-6), a pro-inflammatory cytokine.

The chemotactic agent may be interleukin 7 (IL-7), a protein that in humans is encoded by the IL7 gene. IL-7 is a hematopoietic growth factor secreted by stromal cells in the bone marrow and thymus. IL-7 is also produced by keratinocytes, dendritic cells, hepatocytes, neurons, and epithelial cells, but not by normal lymphocytes.

The chemotactic agent may be interleukin 8 (IL-8), a chemokine of the immune system The chemotactic agent may be interleukin 13 (IL-13), a protein that in humans is encoded by the IL13 gene. IL-13 is on chromosome 5q31, with a length of 1.4 kb. IL-13 and IL-4 show 30% sequence similarity and have a similar structure. IL-13 is a cytokine secreted by many cell types, but especially T helper type 2 (Th2) cells; that is, a mediator of allergic inflammation and disease.

The chemotactic agent may be interleukin 12 (IL-12), an interleukin naturally produced by dendritic cells, macrophages, neutrophils, and human B-lymphoblastoid cells (NC-37) in response to antigenic stimulation. IL-12 is involved in the differentiation of naive T cells into Th1 cells. IL-12 is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells and reduces IL-4 mediated suppression of IFN-γ. T cells that produce IL-12 have a coreceptor, CD30, which is associated with IL-12 activity.

The chemotactic agent may be interferon gamma (IFNγ), a dimerized soluble cytokine, and is the only member of the type II class of interferons.

The chemotactic agent may be IFN-α, which are proteins produced by leukocytes. They are involved in an innate immune response against viral infection. The genes responsible for their synthesis come in 13 subtypes called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9. The recombinant type is interferon alfacon-1. The PEGylated types are PEGylated interferon alfa-2a and PEGylated interferon alfa-2b.

The chemotactic agent may be tumor necrosis factor (TNF, tumor necrosis factor alpha, TNFα, cachexin, or cachectin), a cell-signaling protein (cytokine) involved in systemic inflammation. TNFα is one cytokine that makes up the acute phase reaction. TNFα is produced chiefly by activated macrophages, although it can be produced by many other cell types such as CD4+ lymphocytes, NK cells, neutrophils, mast cells, eosinophils, and neurons. TNF primarily regulates immune cells. TNF, being an endogenous pyrogen, can induce fever, apoptotic cell death, cachexia, inflammation, and inhibit tumorigenesis and viral replication and respond to sepsis via IL1 and IL6 producing cells. Dysregulation of TNF production has been implicated in various human diseases, including Alzheimer's disease, cancer, major depression, psoriasis, and inflammatory bowel disease (IBD). Though controversial, studies of depression and IBD are linked to TNF levels. Recombinant TNF is used as an immunostimulant under the INN tasonermin. TNF can be produced ectopically in the setting of malignancy and parallels parathyroid hormone both in causing secondary hypercalcemia and in the cancers with which excessive production is associated.

The chemotactic agent may be CSF1. The chemotactic agent may be CSF1R.

The chemotactic agent may be a granulocyte-macrophage colony-stimulating factor (GM-CSF), also known as colony-stimulating factor 2 (CSF2), a monomeric glycoprotein secreted by macrophages, T cells, mast cells, natural killer cells, endothelial cells, and fibroblasts that functions as a cytokine. The pharmaceutical analogs of naturally occurring GM-CSF are called sargramostim and molgramostim. Unlike the granulocyte colony-stimulating factor, which specifically promotes neutrophil proliferation and maturation, GM-CSF affects more cell types, especially macrophages and eosinophils.

The immune-modulating therapy may be chemotherapeutic immune stimulation chosen from cyclophosphamide, paclitaxel, doxorubicin, TDO2, IDO, ARG1, ARG2, PDE5, P2X7 inhibitor, P2Y11 inhibitor, A2A Receptor inhibitor, A2B Receptor inhibitor, COX2 inhibitor, EP2 receptor antagonist, EP4 receptor antagonist, RON kinase inhibitor, an ALK5 kinase inhibitor, CSF1 kinase inhibitor, PI3K delta kinase inhibitor, P13K gamma kinase inhibitor, BRAF V600E kinase inhibitor, arginase, and iNOS. IDO is indoleamine 2,3-dioxygenase, a key enzyme of tryptophan metabolism.

The immune-modulating therapy may be radiotherapeutic immune stimulation chosen from gamma irradiation, external beam radiotherapy, stereotactic radiotherapy, radiosurgery, virtual simulation, 3-dimensional conformal radiation therapy, intensity-modulated radiation therapy, intensity-modulated radiation therapy (IMRT), volumetric modulated arc therapy (VMAT), particle therapy, proton beam therapy, auger therapy, brachytherapy, intraoperative radiotherapy, radioisotope therapy, and beta irritation.

Immune-modulating therapy may be a vaccine for TLR4 or TLR9. The vaccine may be toll-like receptor 4 (TLR4). The vaccine may be toll-like receptor 9 (TLR9).

The method may further comprise assessing whether a lymphatic system in a subject is dysregulated. Any method described herein may be used to assess the functioning of the lymphatic system.

C. Cancer

Certain tumor cell types as a group have consistently shown poor response to immune therapies in prospective clinical studies. These so-called "non-responder tumor types" include prostate, colon, breast, and other cancers. Even more, of those tumor cell types that have been shown to respond, such as non-small cell lung cancer (NSCLC), melanoma, urothelial, renal cell, head and neck cancers, only small subsets of patients within these tumors classes have shown responses receiving a true benefit in overall survival (OS). In contrast, the remaining 75% or so do not respond (the so-called "non-responder patients"). For example, in NSCLC, only 25-30% receive a strong benefit (the "responders"). Of the remaining 75% "non-responder patients," 10% have hyperprogession, who rapidly progress on immune therapy within 8 to 12 weeks. The remaining 50% derive no significant benefit beyond standard therapies.

Surprisingly, the present disclosure teaches these "non-responder tumor types" and "non-responder patients" harbor high associations with lymphatic dysfunction (LD), such as lymphangitic carcinomatosis (LC). Moreover, LD and LC are stronger predictors of response than are PD-1 or PD-L1 status in patients with cancer treated with immune therapies, such as checkpoint inhibitors. Contrary to the art, these therapies can be used to treat patients independent of PD-1/PD-L1 status. Further, in patients with low PD-1/PD-L1 status that have been traditionally shown to not benefit from immune therapy, these patients do respond when stratified by LD/LC status alone. Thus, the present disclosure provides that by stratifying by LD alone as the single most influential factor or in combination with PD-1/PD-L1 status or other markers, (a) patients with low PD-1/PD-L1 can be treated effectively with outcomes comparable to those with higher levels of PD-1/PD-L1 status, and (b) tumor types thought to be resistant, even when stratified by high PD-1/L1, respond and benefit from these therapies.

The cancer may be chosen from lung cancer, breast cancer, a cancer of the gastrointestinal tract, a cancer of unknown origin, head and neck cancer, bladder cancer, prostate cancer, skin cancer, kidney cancer, a primary brain tumor, ocular tumor, sarcoma, a cancer of primary soft tissue, mesenchymal cancer, bone cancer, a tumor of the lymphatic system, and leukemia.

The cancer may be lung cancer chosen from non-small cell lung cancer (NSCLC), squamous cell lung cancer, large cell lung cancer, small cell lung cancer, bronchogenic carcinoma, adenocarcinoma, neuroendocrine lung cancer, and bronchoalveolar lung cancer.

The cancer may be breast cancer chosen from ductal carcinoma in situ (DCIS), invasive ductal carcinoma (IDC), lobular carcinoma (ILC), inflammatory breast cancer, lobular carcinoma in situ (LCIS), male breast cancer, Paget's disease of the nipple, and Phyllodes tumors of the breast. The breast cancer may be invasive ductal carcinoma chosen from tubular carcinoma of the breast, medullary carcinoma of the breast, mucinous carcinoma of the breast, papillary carcinoma of the breast, and cribriform carcinoma of the breast. The cancer may be breast cancer defined by hormone receptor status chosen from estrogen receptor positive, estrogen receptor negative, progesterone receptor positive, progesterone receptor negative, herceptin positive, herceptin negative, and combinations thereof. The cancer may be breast cancer defined by the expression of a predefined set of genes chosen from mammaprint, oncotypeDX, intrinsic subtypes, and nanostring prosigna.

The cancer may be a cancer of the gastrointestinal tract chosen from a tumor of the stomach, gastric cancer, duodenal cancer, small or large intestine cancer, colorectal cancer, anal cancer, liver cancer, pancreatic cancer, gall bladder cancer, cholangiocarcinoma, and neuroendocrine cancer.

The cancer may be a skin cancer chosen from basal cell cancer, squamous cell cancer, and melanoma.

The cancer may be kidney cancer chosen from renal cell cancer and oncocytoma.

The cancer may be a primary brain tumor, chosen from glioma, a tumor with gliomatous components, a tumor with neuronal components, a tumor with oligodendroglial components, oligodendroglioma, astrocytoma, and glioblastoma multiforme.

The cancer may be a tumor of the lymphatic system selected from the group consisting of B cell lymphoma, T cell lymphoma, diffuse B cell lymphoma, and Hodgkin's lymphoma.

The cancer may be leukemia chosen from acute lymphoblastic leukemia, acute myeloid leukemia, chronic lymphocytic leukemia, and chronic myelogenous leukemia.

The cancer may be lung cancer, and the method further may comprise administering one or more drugs chosen from afatinib dimaleate, alectinib, bevacizumab, carboplatin, ceritinib, crizotinib, docetaxel, doxorubicin, erlotinib, etoposide, everolimus, gefitinib, gemcitabine, mechlorethamine, methotrexate, necitumumab, nivolumab, osimertinib, paclitaxel, paclitaxel albumin-stabilized nanoparticles, pembrolizumab, pemetrexed, ramucirumab, topotecan, vinorelbine, pharmaceutically acceptable salts thereof, and combinations thereof.

The cancer may be advanced cancer or metastatic cancer.

D. Chemotherapeutic Agents

The methods described herein may be conducted in combination with administering one or more chemotherapeutic agents. Non-limiting examples of chemotherapeutic compounds which can be used in combination treatments include, for example, aminoglutethimide, amsacrine, anastrozole, asparaginase, BCG, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, campothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abcizimab; antimigratory agents; antisecretory agents (breveldin); immunosuppressives (cyclosporine, tacrolimus (FK-506), sirolimus (rapamycin), azathioprine, mycophenolate mofetil); antiangiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, campothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

The cancer may be lung cancer, such as non-small cell lung cancer (NSCLC). Suitable drugs for treated non-small cell lung cancer include, but are not limited to, Abitrexate™ (methotrexate), Abraxane™ (paclitaxel albumin-stabilized nanoparticles), Afinitor™ (everolimus), Alecensa™ (alectinib), Alimta™ (pemetrexed disodium), Avastin™ (bevacizumab), Cyramza™ (ramucirumab), Folex™ (methotrexate), Gilotrif™ (afatinib dimaleate), Gemzar™ (gemcitabine hydrochloride), Iressa™ (gefitinib), Keytruda™ (pembrolizumab), Mexate™ (methotrexate), Mustargen™ (mechlorethamine hydrochloride), Navelbine™ (vinorelbine tartrate), Opdivo™ (nivolumab), Paraplat™ (carboplatin), Paraplatin™ (carboplatin), Portrazza™ (necitumumab), Tagrisso™, (osimertinib), Tarceva™ (erlotinib hydrochloride), Taxol™ (paclitaxel), Taxotere™ (docetaxel), Xalkori™ (crizotinib), and Zykadia™ (ceritinib). Suitable drug combinations for treating non-small cell lung cancer include, but are not limited to, carboplatin and taxol, and gemcitabine, and cisplatin.

Suitable drugs for treating small cell lung cancer include, but are not limited to, Abitrexate™ (methotrexate), Afinitor™ (everolimus), doxorubicin hydrochloride, Etopophos™ (etoposide phosphate), etoposide, Folex™ (methotrexate), Hycamtin™ (topotecan hydrochloride), Mexate™ (methotrexate), and Mustargen™ mechlorethamine hydrochloride).

Pharmaceutical compounds that can be used in combination with a VEGFR-3 and a cancer immune-modulating therapy such as an immune checkpoint inhibitor and (0) VEGFR-2 antagonist include, for example, (1) inhibitors of release of "angiogenic molecules," such as bFGF (basic fibroblast growth factor); (2) neutralizers of angiogenic molecules, such as anti-ObHGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, alpha interferon, and the like.

E. Angiogenesis Inhibitors

The methods described herein may be conducted in combination with administering one or more angiogenesis inhibitors. Compounds that inhibit angiogenesis include, for example, endostatin protein or derivatives, lysine binding fragments of angiostatin, melanin or melanin-promoting compounds, plasminogen fragments (e.g., Kringles 1-3 of plasminogen), troponin subunits, antagonists of vitronectin, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone, and its analogs, and naaladase inhibitors.

Depending on the combinatory therapy, administration of the polypeptide therapeutic agents may be continued while the other therapy is administered and/or thereafter. Administration of the therapeutic agents can be made in a single dose or multiple doses. In some instances, the administration of the therapeutic agents can begin at least several days before the conventional therapy. In contrast, in other instances, the administration can begin either immediately before or at the time of administering conventional therapy.

Although the disclosure described herein is susceptible to various modifications and alternative iterations, specific embodiments thereof have been described in greater detail above. It should be understood, however, that the detailed description of the composition is not intended to limit the disclosure to the specific embodiments disclosed. Rather, the disclosure is intended to cover all modifications, equivalents, and alternatives falling within the spirit and scope of the disclosure as defined by the claim language.

Definitions

The compounds described herein have asymmetric centers. Compounds of the present disclosure having an asymmetrically substituted atom may be isolated in optically active or racemic form. All chiral, diastereomeric, racemic forms and all isomeric geometric forms of a structure are intended unless the specific stereochemistry or isomeric form is specifically indicated.

"Inhibiting an established tumor metastasis" refers to decreasing the size and/or rate of growth of metastasis that has already been established. Established metastases include metastases in lymph nodes (regional metastases) and distant organs (systemic metastases).

"Lymphangiogenesis" refers to the growth of new lymphatic vessels.

"Therapeutically effective" applied to dose or amount refers to that quantity of a pharmaceutical composition sufficient to result in a desired therapeutic activity upon administration to a subject in need thereof, or sufficient to reduce or eliminate at least one symptom of the disease being treated.

"Subject" means any animal, including mammals. The term may refer to a human, a non-human primate, a bovine, an ovine, an equine, a porcine, a canine, a feline, or a rodent (mouse or rat).

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be other elements other than the listed elements.

Having described the disclosure in detail, it will be apparent that modifications and variations are possible without departing from the scope of the disclosure defined in the appended claims.

Examples

The following examples are included to show certain embodiments of the disclosure. It should be appreciated by those of skill in the art that the techniques disclosed in the examples represent techniques discovered by the inventors to function well in the practice of the disclosure. Those of skill in the art should, however, considering the present disclosure, appreciate that many changes can be made in the specific embodiments disclosed and still obtain a like or similar result without departing from the spirit and scope of the disclosure; therefore, all matter set forth is to be interpreted as illustrative and not in a limiting sense.

Tumors responded to checkpoint inhibition based upon lymphatic dysfunction, independent of PD-1/L1, DNA mismatch repair status, microsatellite instability status, or hypermutant status/tumor neoantigen burden.

Patients with advanced or metastatic lung cancer were treated with an inhibitor of PD-1. Patients with a low or negative PD-L1 tumor proportion score (TPS) were evaluated as specified by the drug label, and thus not indicated for the drug and not expected to respond. Their lymphatic systems were evaluated for dysfunction. In one instance, lymphatic system evaluation was performed with serum measurements of VEGF C, VEGF D, or heparin-binding factor midkine in patients before therapy or during treatment. In other instances, the dysfunction was measured with pre-treatment imaging studies and/or similar imaging across the treatment with immunotherapy therapy, including computed tomography, MRI, and nuclear medicine tests, including PET imaging or ventilation perfusion scan.

Evaluating objective measures of response in these patients based on progression-free survival, overall survival, and durable and objective response (RECIST 1.1) and by immune-related response criteria (irRC) confirmed that patients with dysregulated lymphatic systems (designated as "Biomarker Positive" groups) did significantly worse across all these objective measures (overall survival, progression-free survival, objective response, and durable clinical response).

Keytruda™'s product label teaches to the contrary. Pembrolizumab (formerly MK-3475 and lambrolizumab, trade name Keytruda™) is a humanized antibody used in cancer immunotherapy. It blocks a protective mechanism on cancer cells and allows the immune system to destroy those cancer cells. It targets the programmed cell death 1 (PD-1) receptor. It is indicated for patients with metastatic NSCLC, whose tumors have high PD-L1 expression with a tumor proportion score (TPS) of at least 50%, as determined by an FDA-approved test, with no epidermal growth factor receptor (EGFR) or anaplastic lymphoma kinase (ALK). Keytruda™ is also indicated for patients with metastatic NSCLC, whose tumors express PD-L1 (TPS of at least 1%), as determined by an FDA-approved test, with disease progression on or after platinum-containing chemotherapy. That is, the art teaches that patients with low PD-L1 levels cannot be treated.

Opdivo™ is a programmed death receptor-1 (PD-1) blocking antibody. Also known as, nivolumab is indicated for adult and pediatric (12 years and older) patients with microsatellite instability-high (MSI-H) or mismatch repair deficient (dMMR) metastatic colorectal cancer that has progressed following treatment with fluoropyrimidine, oxaliplatin, and irinotecan. Again, the art teaches that patients with low PD-L1 levels cannot be treated.

However, contrary to teaching in the art, patients without a dysregulated lymphatic system, yet who were not expected to respond based on their PD-L1 TPS, had a striking response to the therapy with a significant duration of overall and progression-free survival, thus confirming that the lymphatic system critically determined response to immune checkpoint therapy.

Further, statistical analysis showed that the presence of a dysregulated lymphatic system in this cohort was the single strongest factor for predicting response, outweighing other known important prognostic and predictive factors including age, race, immunotherapy dosing, total tumor burden, gender, smoking, and mutation status, and lung cancer cell type. Similar results were seen in patients treated with PD-L1 inhibitors, with low neoantigen burdens, hypermutant status, and the tumor types shown not to respond to checkpoint inhibition therapy described above.

Figure 8:
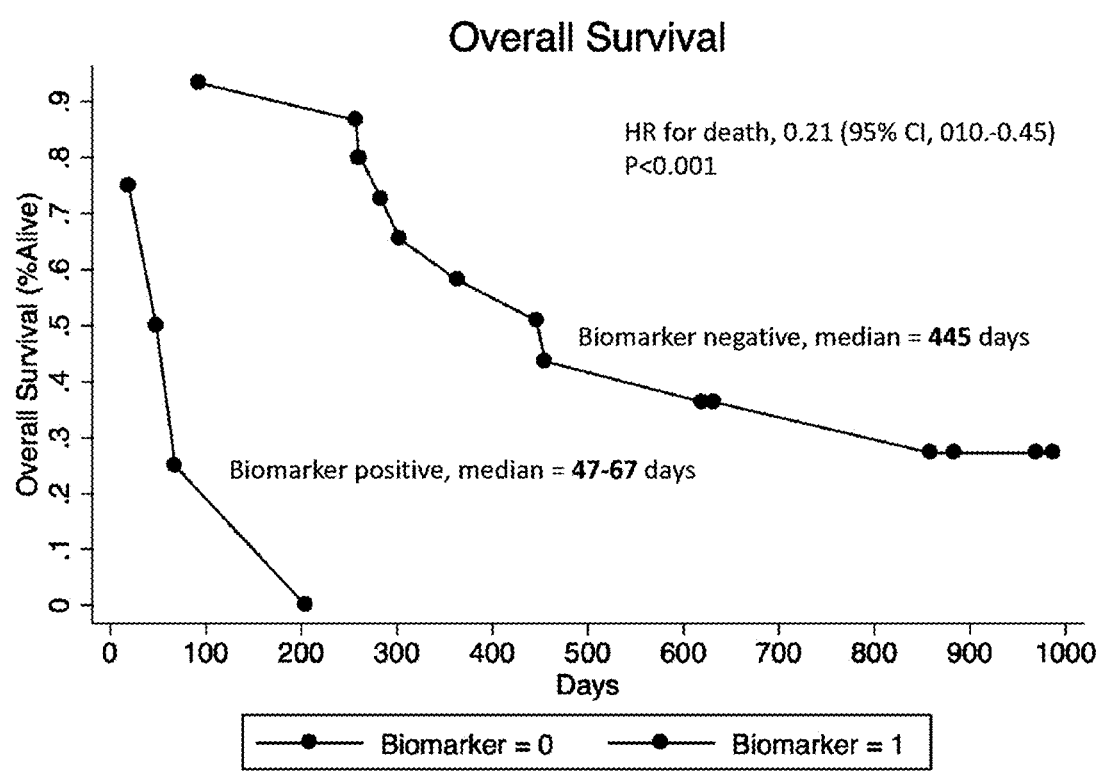
FIG. 8 shows overall survival (% alive) as a function of time in days. Biomarker positive patients survived a median of 47 to 67 days. Biomarker negative patients survived a median of 445 days.

FIG. 8 is a Kaplan Meier plot of Overall Survival (OS) in the subset of NSCLC patients with PD-L1− staining (TPS<1%) showing that patients LC−/PD-L1− derive a significant benefit from the checkpoint inhibitor pembrolizumab compared to the small subset of patients LC+/PD-L1− ($p<0.05$) independent of PD-L1 status/TPS scoring.

Figure 9:
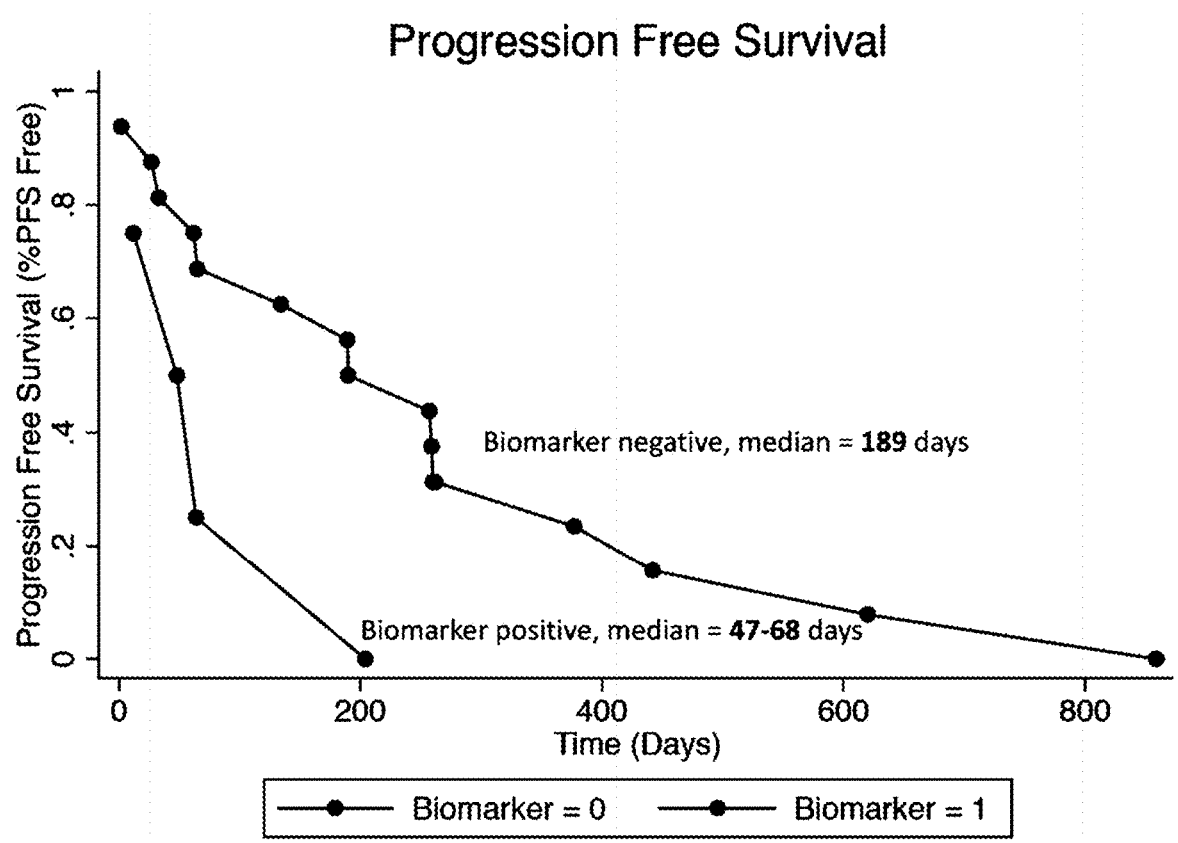
FIG. 9 shows progression-free survival (%) as a function of time in days. Biomarker positive patients had a median survival of 47 to 68 days. Biomarker negative patients had a median survival of 189 days.

FIG. 9 is a Kaplan Meier plot of progression-free survival (PFS) in the subset of NSCLC patients with negative PD-L1 staining (TPS<1%) like FIG. 8. showing that patients LC−/PD-L1− derive a significant PFS benefit from the checkpoint inhibitor pembrolizumab compared to the small subset of patients that LC+/PD-L1− ($p<0.05$). Thus, even in patients that the art (drug label at FIG. 4) teaches will not respond to checkpoint inhibition (low or no PD-L1 staining), derive significant clinical benefits in PFS independent of PD-L1 status, as deemed by the more powerful and independent LC status.

Thus, dysregulated lymphatic systems were a powerful predictor of response to immune-modulating therapies independent of the art, which teaches that PD-L1/PD-1 TPS and hypermutant/neoantigen status were critical determinants of response. Certain tumor types, such as triple-negative breast cancer, colon, pancreatic, glioblastoma multiforme (GBM), prostate cancer, inflammatory, and ER+/HER2+ breast cancers, did not respond well to these therapies.

While specific embodiments have been described above regarding the disclosed embodiments and examples, such embodiments are only illustrative and do not limit the scope of the disclosure. Changes and modifications can be made following ordinary skill in the art without departing from the disclosure in its broader aspects as defined in the following claims.

What is claimed is:

1. A method for treating cancer in a patient in need thereof, comprising selecting a patient having a tumor proportion score for programmed death receptor-1 (PD-1) or programmed death-ligand-1 (PD-L1) from 30% to 0% and being negative for lymphangitic carcinomatosis (LC); and administering to the selected patient a treatment consisting of a therapeutically effective amount of nivolumab or pembrolizumab or a salt thereof, and at least one pharmaceutical excipient.

2. The method of claim 1, wherein the treatment consists of a therapeutically effective amount of pembrolizumab or a salt thereof and at least one pharmaceutical excipient.

3. The method of claim 1, wherein the cancer is lung cancer chosen from non-small cell lung cancer (NSCLC), squamous cell lung cancer, large cell lung cancer, small cell lung cancer, bronchogenic carcinoma, adenocarcinoma, neuroendocrine lung cancer, and bronchoalveolar lung cancer.

4. The method of claim 1, wherein the lung cancer is advanced cancer or metastatic cancer.

5. A method for treating lung cancer in a patient in need thereof, comprising selecting a patient having a tumor proportion score for programmed death receptor-1 (PD-1) or programmed death-ligand-1 (PD-L1) from 30% to 0% and being negative for lymphangitic carcinomatosis (LC); and administering to the selected patient a treatment consisting of a therapeutically effective amount of pembrolizumab or a pharmaceutically acceptable salt thereof and at least one pharmaceutical excipient.

6. The method of claim 5, wherein the cancer is lung cancer chosen from non-small cell lung cancer (NSCLC), squamous cell lung cancer, large cell lung cancer, small cell lung cancer, bronchogenic carcinoma, adenocarcinoma, neuroendocrine lung cancer, and bronchoalveolar lung cancer.

7. The method of claim 1, wherein the treatment is administered to a site of metastasis, a tumor, or a lymph node in the patient.

8. The method of claim 7, wherein the tumor is the primary tumor.

9. The method of claim 7, wherein the lymph node is a primary or secondary draining node.

10. The method of claim 7, wherein an established tumor metastasis is inhibited.

11. The method of claim 7, wherein an established metastatic disease is treated.

12. The method of claim 1, wherein the TPS is from 10% to 0%.

13. The method of claim 1, wherein the TPS is between 1% and 0%.

14. The method of claim 1, wherein the cancer is chosen from lung cancer, breast cancer, a cancer of the gastrointestinal tract, a cancer of unknown origin, head and neck cancer, bladder cancer, prostate cancer, skin cancer, kidney cancer, a primary brain tumor, ocular tumor, sarcoma, a cancer of primary soft tissue, mesenchymal cancer, bone cancer, ovarian cancer, cervical cancer, a tumor of the lymphatic system, leukemia, mismatch repair deficient positive tumors (MMRD positive), mismatch repair deficient negative tumors (MMRD negative), and microsatellite (MSI) instability positive or negative cancers.

15. The method of claim 10, wherein the cancer is breast cancer chosen from ductal carcinoma in situ (DCIS), invasive ductal carcinoma (IDC), lobular carcinoma (ILC), inflammatory breast cancer, lobular carcinoma in situ (LCIS), male breast cancer, Paget's disease of the nipple, and Phyllodes tumors of the breast.

16. The method of claim 11, wherein the breast cancer is invasive ductal carcinoma chosen from tubular carcinoma of the breast, medullary carcinoma of the breast, mucinous carcinoma of the breast, papillary carcinoma of the breast, and cribriform carcinoma of the breast.

17. The method of claim 10, wherein the cancer is breast cancer defined by hormone receptor status chosen from estrogen receptor positive, estrogen receptor negative, progesterone receptor positive, progesterone receptor negative, herceptin positive, herceptin negative, and combinations thereof.

18. The method of claim 10, wherein the cancer is breast cancer defined by expression of a pre-defined set of genes chosen from mammaprint, oncotypeDX, intrinsic subtypes, and nanostring prosigna.

19. The method of claim 10, wherein the cancer is a cancer of the gastrointestinal tract chosen from a tumor of the stomach, gastric cancer, duodenal cancer, small or large intestine cancer, colorectal cancer, anal cancer, liver cancer, pancreatic cancer, gall bladder cancer, cholangiocarcinoma, and neuroendocrine cancer.

20. The method of claim 10, wherein the cancer is a skin cancer chosen from basal cell cancer, squamous cell cancer, and melanoma.

21. The method of claim 10, wherein the cancer is kidney cancer chosen from renal cell cancer, papillary, and oncocytoma.

22. The method of claim 10, wherein the cancer is a primary brain tumor, chosen from glioma, a tumor with gliomatous components, a tumor with neuronal components, a tumor with oligodendroglial components, oligodendroglioma, astrocytoma, and glioblastoma multiforme.

23. The method of claim 10, wherein the cancer is a tumor of the lymphatic system selected from the group consisting of B cell lymphoma, T cell lymphoma, diffuse B cell lymphoma, and Hodgkin's lymphoma.

24. The method of claim 10, wherein the cancer is leukemia chosen from acute lymphoblastic leukemia, acute myeloid leukemia, chronic lymphocytic leukemia, and chronic myelogenous leukemia.

25. The method of claim 1, further comprising determining cancer in a patient for a tumor proportion score for programmed death receptor-1 (PD-1) or programmed death-ligand-1 (PD-L1).

26. The method of claim 1, further comprising determining the patient for lymphangitic carcinomatosis (LC).

* * * * *